US010117613B2

(12) United States Patent
Wisniewski et al.

(10) Patent No.: US 10,117,613 B2
(45) Date of Patent: Nov. 6, 2018

(54) TISSUE-INTEGRATING SENSORS

(71) Applicant: Profusa, Inc., San Francisco, CA (US)

(72) Inventors: Natalie A. Wisniewski, San Francisco, CA (US); Kristen Helton, Seattle, WA (US); William A. McMillan, La Honda, CA (US)

(73) Assignee: Profusa, Inc., South San Francisco, CA (US)

( * ) Notice: Subject to any disclaimer, the term of this patent is extended or adjusted under 35 U.S.C. 154(b) by 0 days.

(21) Appl. No.: 15/087,514

(22) Filed: Mar. 31, 2016

(65) Prior Publication Data

US 2016/0213288 A1    Jul. 28, 2016

Related U.S. Application Data

(63) Continuation of application No. 13/267,741, filed on Oct. 6, 2011.

(60) Provisional application No. 61/390,252, filed on Oct. 6, 2010.

(51) Int. Cl.
*A61B 5/1455* (2006.01)
*A61B 5/1459* (2006.01)
*A61B 5/145* (2006.01)
*A61B 5/1473* (2006.01)
*A61B 5/1495* (2006.01)
*A61B 5/00* (2006.01)

(52) U.S. Cl.
CPC .......... *A61B 5/1459* (2013.01); *A61B 5/0004* (2013.01); *A61B 5/0017* (2013.01); *A61B 5/0031* (2013.01); *A61B 5/1495* (2013.01); *A61B 5/14503* (2013.01); *A61B 5/14532* (2013.01); *A61B 5/14735* (2013.01); *A61B 5/681* (2013.01); *A61B 5/7278* (2013.01)

(58) Field of Classification Search
None
See application file for complete search history.

(56) References Cited

U.S. PATENT DOCUMENTS

| 4,703,756 | A | 11/1987 | Gough et al. |
| 5,001,054 | A | 3/1991 | Wagner |
| 5,161,532 | A | 11/1992 | Joseph |
| 5,284,140 | A | 2/1994 | Allen et al. |
| 5,342,789 | A | 8/1994 | Chick et al. |
| 5,512,246 | A | 4/1996 | Russell et al. |
| 5,551,422 | A | 9/1996 | Simonsen et al. |
| 5,777,060 | A | 7/1998 | Van Antwerp |
| 5,895,658 | A | 4/1999 | Fossel |

(Continued)

FOREIGN PATENT DOCUMENTS

| CN | 1675547 A | 9/2005 |
| CN | 1882278 A | 12/2006 |

(Continued)

OTHER PUBLICATIONS

Examination Report for Australian Application No. 2011311889, dated Dec. 20, 2013.

(Continued)

*Primary Examiner* — Eric Winakur
*Assistant Examiner* — Marjan Fardanesh

(57) ABSTRACT

Tissue-integrating biosensors, systems comprising these sensors and methods of using these sensors and systems for the detection of one or more analytes are provided.

28 Claims, 18 Drawing Sheets

(56) References Cited

U.S. PATENT DOCUMENTS

| | | | |
|---|---|---|---|
| 5,962,852 A | 10/1999 | Knuettel et al. |
| 6,002,954 A | 12/1999 | Van Antwerp et al. |
| 6,011,984 A | 1/2000 | Van Antwerp et al. |
| 6,013,122 A | 1/2000 | Klitzman et al. |
| 6,040,194 A | 3/2000 | Chick et al. |
| 6,104,945 A | 8/2000 | Modell et al. |
| 6,175,752 B1 | 1/2001 | Say et al. |
| 6,212,416 B1 | 4/2001 | Ward et al. |
| 6,299,604 B1 | 10/2001 | Ragheb et al. |
| 6,319,540 B1 | 11/2001 | Van Antwerp et al. |
| 6,376,971 B1 | 4/2002 | Pelrine et al. |
| 6,379,622 B1 | 4/2002 | Polak et al. |
| 6,475,750 B1 | 11/2002 | Han et al. |
| 6,485,703 B1 | 11/2002 | Cote et al. |
| 6,497,729 B1 | 12/2002 | Moussy et al. |
| 6,543,110 B1 | 4/2003 | Pelrine et al. |
| 6,565,509 B1 | 5/2003 | Say et al. |
| 6,565,960 B2 | 5/2003 | Koob et al. |
| 6,583,533 B2 | 6/2003 | Pelrine et al. |
| 6,602,678 B2 | 8/2003 | Kwon et al. |
| 6,642,015 B2 | 11/2003 | Vachon et al. |
| 6,671,527 B2 | 12/2003 | Petersson et al. |
| 6,702,857 B2 | 3/2004 | Brauker et al. |
| 6,750,311 B1 | 6/2004 | Van Antwerp et al. |
| 6,766,183 B2 | 7/2004 | Walsh et al. |
| 6,794,195 B2 | 9/2004 | Colvin, Jr. |
| 6,804,544 B2 | 10/2004 | Van Antwerp et al. |
| 6,818,226 B2 | 11/2004 | Reed et al. |
| 6,821,530 B2 | 11/2004 | Koob et al. |
| 6,844,023 B2 | 1/2005 | Schulman et al. |
| 6,858,184 B2 | 2/2005 | Pelrine et al. |
| 6,916,660 B2 | 7/2005 | Wang et al. |
| 6,927,246 B2 | 8/2005 | Noronha et al. |
| 6,965,791 B1 | 11/2005 | Hitchcock et al. |
| 6,994,691 B2 | 2/2006 | Ejlersen |
| 7,045,361 B2 | 5/2006 | Heiss et al. |
| 7,060,503 B2 | 6/2006 | Colvin, Jr. |
| 7,067,194 B2 | 6/2006 | Mao et al. |
| 7,110,803 B2 | 9/2006 | Shults et al. |
| 7,132,049 B2 | 11/2006 | Hou et al. |
| 7,134,999 B2 | 11/2006 | Brauker et al. |
| 7,153,265 B2 | 12/2006 | Vachon |
| 7,162,289 B2 | 1/2007 | Shah et al. |
| 7,186,789 B2 | 3/2007 | Hossainy et al. |
| 7,192,450 B2 | 3/2007 | Brauker et al. |
| 7,202,947 B2 | 4/2007 | Liu et al. |
| 7,226,978 B2 | 6/2007 | Tapsak et al. |
| 7,228,159 B2 | 6/2007 | Petersson et al. |
| 7,406,345 B2 | 7/2008 | Muller et al. |
| 7,424,317 B2 | 9/2008 | Parker et al. |
| 7,450,980 B2 | 11/2008 | Kawanishi |
| 7,468,575 B2 | 12/2008 | Pelrine et al. |
| 7,496,392 B2 | 2/2009 | Alarcon et al. |
| 7,521,019 B2 | 4/2009 | Polak et al. |
| 7,541,598 B2 | 6/2009 | Aasmul |
| 7,567,347 B2 | 7/2009 | Aasmul |
| 7,629,172 B2 | 12/2009 | Alarcon et al. |
| 7,653,424 B2 | 1/2010 | March |
| 7,704,704 B2 | 4/2010 | Ibey et al. |
| 7,772,286 B2 | 8/2010 | Muller et al. |
| 7,869,853 B1 | 1/2011 | Say et al. |
| 7,923,064 B2 | 4/2011 | Pelrine et al. |
| 7,927,519 B2 | 4/2011 | Domschke et al. |
| 7,939,332 B2 | 5/2011 | Colvin, Jr. |
| 7,972,628 B2 | 7/2011 | Ratner et al. |
| 8,008,088 B2 | 8/2011 | Bellott et al. |
| 8,057,041 B2 | 11/2011 | Muller et al. |
| 8,088,595 B2 | 1/2012 | Ibey et al. |
| 8,131,333 B2 | 3/2012 | Chapoy et al. |
| 8,206,622 B2 | 6/2012 | Kammermeier et al. |
| 8,318,193 B2 | 11/2012 | Ratner et al. |
| 8,346,337 B2 | 1/2013 | Heller et al. |
| 8,346,363 B2 | 1/2013 | Darvish et al. |
| 8,368,556 B2 | 2/2013 | Sicurello et al. |
| 8,372,423 B2 | 2/2013 | Marshall et al. |
| 8,372,630 B2 | 2/2013 | Uematsu et al. |
| 8,382,700 B2 | 2/2013 | Straessler et al. |
| 8,385,998 B2 | 2/2013 | Zhang et al. |
| 8,394,463 B1 | 3/2013 | Chiu et al. |
| 8,423,114 B2 | 4/2013 | Simpson et al. |
| 8,452,361 B2 | 5/2013 | Muller |
| 8,452,363 B2 | 5/2013 | Muller et al. |
| 8,460,231 B2 | 6/2013 | Brauker et al. |
| 8,465,425 B2 | 6/2013 | Heller et al. |
| 8,483,793 B2 | 7/2013 | Simpson et al. |
| 8,508,109 B2 | 8/2013 | Pelrine et al. |
| 8,512,245 B2 | 8/2013 | Markle et al. |
| 8,527,025 B1 | 9/2013 | Shults et al. |
| 8,527,026 B2 | 9/2013 | Shults et al. |
| 8,535,262 B2 | 9/2013 | Markle et al. |
| 8,543,182 B2 | 9/2013 | Botvinick et al. |
| 8,543,184 B2 | 9/2013 | Boock et al. |
| 8,543,354 B2 | 9/2013 | Luo et al. |
| 8,579,879 B2 | 11/2013 | Palerm et al. |
| 8,608,924 B2 | 12/2013 | Cooper et al. |
| RE44,695 E | 1/2014 | Simpson et al. |
| 8,622,903 B2 | 1/2014 | Jin et al. |
| 8,623,639 B2 | 1/2014 | Amiss et al. |
| 8,628,471 B2 | 1/2014 | Mazar et al. |
| 8,647,271 B2 | 2/2014 | Muller et al. |
| 8,647,393 B2 | 2/2014 | Marshall et al. |
| 8,666,471 B2 | 3/2014 | Rogers |
| 8,927,022 B2 | 1/2015 | Maginness et al. |
| 8,940,544 B2 | 1/2015 | Suri et al. |
| 8,945,942 B2 | 2/2015 | Herbrechtsmeier et al. |
| 9,244,064 B2 | 1/2016 | Muller et al. |
| 9,826,926 B2 | 11/2017 | Muller et al. |
| 2002/0043651 A1 | 4/2002 | Darrow et al. |
| 2002/0048577 A1 | 4/2002 | Bornstein et al. |
| 2002/0050769 A1 | 5/2002 | Pelrine et al. |
| 2002/0094526 A1* | 7/2002 | Bayley ............... C07K 14/31 435/6.19 |
| 2002/0106314 A1 | 8/2002 | Pelrine et al. |
| 2002/0193672 A1 | 12/2002 | Walsh et al. |
| 2003/0004554 A1 | 1/2003 | Riff et al. |
| 2003/0050542 A1 | 3/2003 | Reihl et al. |
| 2003/0088682 A1 | 5/2003 | Hlasny |
| 2003/0099682 A1 | 5/2003 | Moussy et al. |
| 2003/0153026 A1 | 8/2003 | Alarcon et al. |
| 2003/0171666 A1 | 9/2003 | Loeb et al. |
| 2003/0208166 A1 | 11/2003 | Schwartz |
| 2004/0106951 A1 | 6/2004 | Edman et al. |
| 2004/0143221 A1 | 7/2004 | Shadduck |
| 2004/0161853 A1 | 8/2004 | Yang et al. |
| 2004/0176669 A1 | 9/2004 | Colvin, Jr. |
| 2004/0195528 A1 | 10/2004 | Reece et al. |
| 2004/0234962 A1 | 11/2004 | Alarcon et al. |
| 2004/0258732 A1* | 12/2004 | Shikinami ........... A61L 27/446 424/426 |
| 2004/0259270 A1 | 12/2004 | Wolf |
| 2005/0027175 A1 | 2/2005 | Yang |
| 2005/0095174 A1 | 5/2005 | Wolf |
| 2005/0096587 A1 | 5/2005 | Santini, Jr. et al. |
| 2005/0118726 A1 | 6/2005 | Schultz et al. |
| 2005/0119737 A1 | 6/2005 | Bene et al. |
| 2005/0154374 A1 | 7/2005 | Hunter et al. |
| 2005/0182389 A1 | 8/2005 | LaPorte et al. |
| 2005/0237518 A1 | 10/2005 | Colvin, Jr. et al. |
| 2005/0245799 A1 | 11/2005 | Brauker et al. |
| 2006/0002890 A1* | 1/2006 | Hersel ............... A61K 31/785 424/78.27 |
| 2006/0002969 A1 | 1/2006 | Kyriakides et al. |
| 2006/0089548 A1 | 4/2006 | Hogan |
| 2006/0148983 A1 | 7/2006 | Muller et al. |
| 2006/0155179 A1 | 7/2006 | Muller et al. |
| 2006/0252976 A1 | 11/2006 | Rosero |
| 2006/0270919 A1 | 11/2006 | Brenner |
| 2006/0275340 A1 | 12/2006 | Udipi et al. |
| 2006/0289307 A1 | 12/2006 | Yu et al. |
| 2007/0002470 A1 | 1/2007 | Domschke et al. |
| 2007/0004046 A1* | 1/2007 | Abbott ............... B82Y 15/00 436/104 |
| 2007/0010702 A1 | 1/2007 | Wang et al. |
| 2007/0030443 A1 | 2/2007 | Chapoy et al. |

(56) References Cited

U.S. PATENT DOCUMENTS

| | | |
|---|---|---|
| 2007/0093617 A1 | 4/2007 | DesNoyer et al. |
| 2007/0105176 A1 | 5/2007 | Ibey et al. |
| 2007/0134290 A1 | 6/2007 | Rowland et al. |
| 2007/0135698 A1 | 6/2007 | Shah et al. |
| 2007/0244379 A1 | 10/2007 | Boock et al. |
| 2007/0270675 A1 | 11/2007 | Kane et al. |
| 2008/0020012 A1 | 1/2008 | Ju et al. |
| 2008/0075752 A1 | 3/2008 | Ratner et al. |
| 2008/0136052 A1 | 6/2008 | Pelrine et al. |
| 2008/0139903 A1 | 6/2008 | Bruce et al. |
| 2008/0191585 A1 | 8/2008 | Pelrine et al. |
| 2008/0249381 A1 | 10/2008 | Muller et al. |
| 2009/0005663 A1 | 1/2009 | Parker et al. |
| 2009/0131773 A1 | 5/2009 | Struve et al. |
| 2009/0187084 A1 | 7/2009 | Kristensen et al. |
| 2009/0221891 A1 | 9/2009 | Yu et al. |
| 2009/0270953 A1 | 10/2009 | Ecker et al. |
| 2010/0113901 A1 | 5/2010 | Zhang et al. |
| 2010/0123121 A1 | 5/2010 | Taylor |
| 2010/0160749 A1 | 6/2010 | Gross et al. |
| 2010/0185066 A1 | 7/2010 | March |
| 2010/0222657 A1 | 9/2010 | Ibey et al. |
| 2010/0249548 A1 | 9/2010 | Mueller |
| 2010/0303772 A1 | 12/2010 | McMillan et al. |
| 2010/0305413 A1 | 12/2010 | Paterson |
| 2011/0028806 A1 | 2/2011 | Merritt et al. |
| 2011/0036994 A1* | 2/2011 | Frayling ............. G01N 21/648 250/459.1 |
| 2011/0154641 A1 | 6/2011 | Pelrine et al. |
| 2011/0155307 A1 | 6/2011 | Pelrine et al. |
| 2011/0224514 A1 | 9/2011 | Muller et al. |
| 2011/0230835 A1 | 9/2011 | Muller et al. |
| 2012/0123276 A1 | 5/2012 | Govari et al. |
| 2012/0140094 A1 | 6/2012 | Shpunt et al. |
| 2012/0172692 A1 | 7/2012 | Tamada et al. |
| 2012/0179014 A1 | 7/2012 | Shults et al. |
| 2012/0186581 A1 | 7/2012 | Brauker et al. |
| 2012/0190953 A1 | 7/2012 | Brauker et al. |
| 2012/0191063 A1 | 7/2012 | Brauker et al. |
| 2012/0215201 A1 | 8/2012 | Brauker et al. |
| 2012/0220979 A1 | 8/2012 | Brauker et al. |
| 2012/0238852 A1 | 9/2012 | Brauker et al. |
| 2012/0245445 A1 | 9/2012 | Black et al. |
| 2012/0258551 A1 | 10/2012 | Herbrechtsmeier et al. |
| 2012/0265034 A1 | 10/2012 | Wisniewski et al. |
| 2012/0283538 A1 | 11/2012 | Rose et al. |
| 2012/0296311 A1 | 11/2012 | Brauker et al. |
| 2013/0006069 A1 | 1/2013 | Gil et al. |
| 2013/0022648 A1 | 1/2013 | Maginness et al. |
| 2013/0030273 A1 | 1/2013 | Tapsak et al. |
| 2013/0060105 A1 | 3/2013 | Shah et al. |
| 2013/0158413 A1 | 6/2013 | Lisogurski et al. |
| 2013/0172699 A1 | 7/2013 | Rebec et al. |
| 2013/0211213 A1 | 8/2013 | Dehennis et al. |
| 2013/0213110 A1 | 8/2013 | Papadimitrakopoulos et al. |
| 2013/0213112 A1 | 8/2013 | Stumber |
| 2013/0229660 A1 | 9/2013 | Goldschmidt et al. |
| 2013/0231542 A1 | 9/2013 | Simpson et al. |
| 2013/0302908 A1 | 11/2013 | Amiss et al. |
| 2013/0310666 A1 | 11/2013 | Shults et al. |
| 2013/0310670 A1 | 11/2013 | Boock et al. |
| 2013/0311103 A1 | 11/2013 | Cooper et al. |
| 2013/0313130 A1 | 11/2013 | Little et al. |
| 2013/0337468 A1 | 12/2013 | Muller et al. |
| 2014/0000338 A1 | 1/2014 | Luo et al. |
| 2014/0148596 A1 | 5/2014 | Dichtel et al. |
| 2014/0275869 A1 | 9/2014 | Kintz et al. |
| 2014/0316224 A1 | 10/2014 | Sato |
| 2014/0357964 A1 | 12/2014 | Wisniewski et al. |
| 2014/0364707 A1 | 12/2014 | Kintz et al. |
| 2016/0374556 A1 | 12/2016 | Colvin et al. |
| 2017/0087376 A1 | 3/2017 | McMillan et al. |
| 2017/0325722 A1 | 11/2017 | Wisniewski et al. |

FOREIGN PATENT DOCUMENTS

| | | |
|---|---|---|
| EP | 2517619 B1 | 5/2013 |
| JP | 2004-537344 | 12/2004 |
| JP | 2008/541881 | 11/2008 |
| WO | WO 91/09312 | 6/1991 |
| WO | WO 97/19188 | 5/1997 |
| WO | WO 98/06406 | 2/1998 |
| WO | WO 00/02048 | 1/2000 |
| WO | WO 2001/006579 | 1/2001 |
| WO | WO 01/18543 | 3/2001 |
| WO | WO 2001/075450 | 10/2001 |
| WO | WO 2002/087610 | 11/2002 |
| WO | WO 2003/006992 | 1/2003 |
| WO | WO 2005/059037 | 6/2005 |
| WO | WO 2005/120631 | 12/2005 |
| WO | WO 2006/004595 | 1/2006 |
| WO | WO 2006/044972 | 4/2006 |
| WO | WO 2006/065266 | 6/2006 |
| WO | WO 2006/130461 | 12/2006 |
| WO | WO 2007/065653 | 6/2007 |
| WO | WO 2007/126444 | 11/2007 |
| WO | WO 2008/105791 | 9/2008 |
| WO | WO 2008/141241 | 11/2008 |
| WO | WO 2008/142158 | 11/2008 |
| WO | WO 2008/143651 | 11/2008 |
| WO | WO 2009/019470 | 2/2009 |
| WO | WO 2009/087373 | 7/2009 |
| WO | WO 2009/106805 | 9/2009 |
| WO | WO 2010/037847 | 4/2010 |
| WO | WO 2010/116142 | 10/2010 |
| WO | WO 2010/133831 | 11/2010 |
| WO | WO 2010/141377 | 12/2010 |
| WO | WO 2011/101624 | 8/2011 |
| WO | WO 2011/101625 | 8/2011 |
| WO | WO 2011/101626 | 8/2011 |
| WO | WO 2011/101627 | 8/2011 |
| WO | WO 2011/101628 | 8/2011 |
| WO | WO 2013/073270 | 5/2013 |
| WO | WO 2013/132400 | 9/2013 |
| WO | WO 2014/158988 | 10/2014 |
| WO | WO 2014/160258 | 10/2014 |
| WO | WO 2014/197786 | 12/2014 |

OTHER PUBLICATIONS

Examination Report for Australian Application No. 2011311889, dated May 28, 2014.
Office Action for Chinese Application No. 201180057627.5, dated Dec. 15, 2014.
Notice of Reasons for Rejection for Japanese Application No. 2013-532954, dated Mar. 31, 2015.
International Search Report and Written Opinion for International Application No. PCT/US2011/055157, dated Jan. 23, 2012.
Office Action for U.S. Appl. No. 13/267,741, dated Mar. 20, 2015.
Office Action for U.S. Appl. No. 13/267,741, dated Apr. 1, 2014.
Office Action for U.S. Appl. No. 13/267,741, dated Oct. 7, 2015.
Office Action for U.S. Appl. No. 13/267,741, dated Nov. 20, 2014.
Examination Report for Australian Application No. 2010256930, dated Dec. 18, 2013.
English Translation of Office Action for Korean Patent Application No. 10-2013-7010584, dated Mar. 16, 2016.
Alexeev et al., "High ionic strength glucose-sensing photonic crystal," Anal. Chem., 75:2316-2323 (2003).
Alexeev et al., "Photonic crystal glucose-sensing material for non-invasive monitoring of glucose in tear fluid," Clinical Chemistry, 50(12):2353-2360 (2004).
Aslan et al., "Nanogold plasmon-resonance-based glucose sensing 2: wavelengthratiometric resonance light scattering," Anal. Chem., 77(7):2007-2014 (2005).
Badylak et al., "Immune response to biologic scaffold materials," Seminars in Immunology, 20(2):109-116 (2008).
Ballerstadt et al., "Competitive-binding assay method based on fluorescence quenching of ligands held in close proximity by a multivalent receptor," Anal. Chem., Acta. 345:203-212 (1997).

(56) References Cited

OTHER PUBLICATIONS

Bhardwaj, U. et al., "A review of the development of a vehicle for localized and controlled drug delivery for implantable biosensors," Journal of Diabetes Science and Technology, 2(6):1016-1029 (2008).
Billingsley et al., "Fluorescent nano-optodes for glucose detection," Anal. Chem., 82(9):3707-3713 (2010).
Brasuel et al., "Fluorescent nanosensors for intracellular chemical analysis: decyl methacrylate liquid polymer matrix and ion-exchange-based potassium pebble sensors with real-time application to viable rat C6 glioma cells. " Anal. Chem., 73(10):2221-2228 (2001).
Brasuel et al., "Liquid polymer nano-pebbles for CL-analysis and biological applications," Analyst, 128(10):1262-1267 (2003).
Braun et al., "Comparison of tumor and normal tissue oxygen tension measurements using oxylite or microelectrodes in rodents," Am. J. Physiol. Heart Circ. Physiol., 280(6):H2533-H2544 (2001).
Bridges et al., "Chronic inflammatory responses to microgel-based implant coatings," J Biomed. Mater. Res. A., 94(1):252-258 (2010).
Chaudhary et al., "Evaluation of glucose sensitive affinity binding assay entrapped in fluorescent dissolved-core alginate microspheres," Biotechnology and Bioengineering, 104(6):1075-1085 (2009).
Cordeiro, P.G. et al., "The protective effect of L-arginine on ischemia-reperfusion injury in rat skin flaps," Plast Reconstruct Surg., 100(5):1227-1233 (1997).
Dunphy, I. et al., "Oxyphor R2 and G2: phosphors for measuring oxygen by oxygen-dependent quenching phosphorescence," Anal. Biochem., 310:191-198 (2002).
Garg, S. K. et al., "Improved glucose excursions using an implantable real-time continuous glucose sensor in adults with Type 1 diabetes," Diabetes Care, 27(3):734-738 (2004).
Henninger, N., et al., "Tissue response to subcutaneous implantation of glucose-oxidase-based glucose sensors in rats," Biosens Bioelectron, 23(1):26-34 (2007).
Horgan et al., "Crosslinking of phenylboronic acid receptors as a means of glucose selective holographic detection," Biosensors and Bioelectronics, 21(9):1838-1845 (2006).
Ibey et al., "Competitive binding assay for glucose based on glycodendrimer fluorophore conjugates," Anal. Chem., 77(21):7039-7046 (2005).
Isenhath et al., "A mouse model to evaluate the interface between skin and a percutaneous device," J Biomed. Mater. Research, 83A:915-922 (2007).
Ju, Y. M. et al., "A novel porous collagen scaffold around an implantable biosensor for improving biocompatibility. I. In vitrol in vivo stability of the scaffold and in vitro sensitivity of the glucose sensor with scaffold " J Biomed. Mater. Research. 87A:136-146 (2008), Available online Dec. 17, 2007.
Kaehr et al., "Multiphoton fabrication of chemically responsive protein hydrogels for microactuation," PNAS USA, 105(26):8850-8854 (2008).
Kasprzak, S. E., "Small-scale polymer structures enabled by thiol-ene copolymer systems," Doctoral Dissertation, Georgia Institute of Technology, May 2009.
Klimowicz, A. et al., "Evaluation of skin penetration of topically applied drugs by cutaneous microdialysis:acyclovir vs salicylic acid," J Clin Pharm Ther, 3(2):143-148 (2007).
Kloxin, A. M. et al., "Photodegradable hydrogels for dynamic tuning of physical and chemical properties," Science, 324:59-63 (2009).
Mansouri et al., "A minature optical glucose sensor based on affinity binding," Nature Biotechnology, 23:885-890 (1984).
Marshall et al., "Biomaterials with tightly controlled pore size that promote vascular in-growth," ACS Polymer Preprints, 45(2):100-101 (2004).
McShane et al., "Glucose monitoring using implanted fluorescent microspheres," IEEE Engineering in Medicine and Biology Magazine, 19(6):36-45 (2000).
Nagler, A. et al., "Topical treatment of cutaneous chronic graft versus host disease with halofuginone: a novel inhibitor of collagen Type 1 synthesis," Transplantation, 68(11):1806-1809 (1999).
Nielsen et al., "Clinical evaluation of a transcutaneous interrogated fluorescence lifetime-based microsensor for continuous glucose reading," J Diabetes and Technology, 3(1):98-109 (2009).
Nielson, R. et al., "Microreplication and design of biological architectures using dynamicmask multiphoton lithography," Small, 5(1):120-125 (2009).
Onuki, Y. et al., "A review of the biocompatibility of implantable devices: Current challenges to overcome foreign body response," Journal of Diabetes Science and Technology, 2(6):1003-1015 (2008).
Ostendorf, A. et al., "Two-photon polymerization: a new approach to micromachining," Photonics Spectra, 40(10):72-79 (2006).
Ozdemir et al., "Axial pattern composite prefabrication of high-density porous polyethylene: experimental and clinical research," Plast. Reconstr. Surg., 115(1):183-196 (2005).
Phelps et al., "Bioartificial matrices for therapeutic vascularization," PNAS USA, 107(8):3323-3328 (2010).
Pickup, J. C. et al., "In vivo glucose monitoring: the clinical reality and the promise," Biosens Bioelectron., 20(10):1897-1902 (2005), Available online Oct. 3, 2004.
Rounds et al., "Microporated peg spheres for fluorescent analyte detection," Journal of Fluorescence, 17(1):57-63 (2007), Available online Nov. 17, 2006.
Russell et al., "A fluorescence-based glucose biosensor using concanavalin A and dextran encapsulated in apoly(ethylene glycol) hydrogel," Anal. Chem., 71(15):3126-3132 (1999).
Sanders et al., "Tissue response to single-polymer fibers of varying diameters: evaluation of fibrous encapsulation and macrophage density," J Biomed. Mater. Research, 52:231-237 (2000).
Sanders et al., "Tissue response to microfibers of different polymers: polyester, polyethylene, polylactic acid, and polyurethane," J Biomed. Mater. Research, 62(2):222-227 (2002).
Sanders et al., "Fibrous encapsulation of single polymer microfibers depends on their vertical dimension in subcutaneous tissue," J Biomed. Mater. Research, 67A:1181-1187 (2003).
Sanders et al., "Relative influence of polymer fiber diameter and surface charge on fibrous capsule thickness and vessel density for single-fiber implants," J Biomed. Mater. Research, 65A:462-467 (2003).
Sanders et al., "Polymer microfiber mechanical properties: a system for assessment and investigation of the link with fibrous capsule formation," J Biomed. Mater. Research, 67A:1412-1416 (2003).
Sanders et al., "Small fiber diameter fibro-porous meshes: tissue response sensitivity to fiber spacing," J Biomed Mater Research, 72A:335-342 (2005).
Sanders et al., "Fibro-porous meshes made from polyurethane micro-fibers: effects of surface charge on tissue response," Biomaterials, 26(7):813-818 (2005).
Schultz et al., "Affinity sensor: a new technique for developing implantable sensors for glucose and other metabolites," Diabetes Care, 5(3)245-253 (1982).
Smith, J. L., "The Pursuit of Noninvasive Glucose: 'Hunting the Deceitful Turkey,'" (2006).
Srivastava et al., "Application of self-assembled ultrathin film coatings to stabilize macromolecule encapsulation in alginate microspheres," J of Microencapsulation, 22(4):397-411 (2005).
Srivastava et al., "Stabilization of glucose oxidase in alginate microspheres with photo reactive diazoresin nanofilm coatings," Biotechnology and Bioengineering, 91(1):124-131 (2005).
Takano et al., "An oxo-bacteriochlorin derivative for long-wavelength fluorescence ratiometric alcohol sensing," Analyst, 135:2334-2339 (2010).
Tian et al., "Dually fluorescent sensing of PH and dissolved oxygen using a membrane made from polymerizable sensing monomers," Sensors and Actuators B, 147:714-722 (2010).
Tian et al., "Influence of matrices on oxygen sensing of three-sensing films with chemically conjugated platinum porphyrin probes and preliminary application for monitoring of oxygen consumption of *Escherichia coli* (*E. coli*)," Sensors and Actuators B, 150:579-587 (2010).
Tian, Y. et al., "A New Cross-linkable Oxygen Sensor Covalently Bonded into Poly(2-hydroxyethyl methacrylate)-co-Polyacrylamide Thin Film for Dissolved Oxygen Sensing," Chem. Mater, 22:2069-2078 (2010).

(56) References Cited

OTHER PUBLICATIONS

Vidavalur, R. et al., "Sildenafil induces angiogenic response in human coronary arterioloar endothelial cells through the expression of thioredoxin, hemaoxygenase, and VEGF," Vasc Pharm, 45(2):91-95 (2006).
Ward, W. K. et.al., "The effect of microgeometry, implant thickness and polyurethane chemistry on the foreign body response to subcutaneous implants," Biomaterials, 23(21):4185-4192 (2002).
Wisniewski, N. et.al., "Characterization of implantable biosensor membrane fouling," Fresen J Anal Chem., 366 (6-7):611-621 (2000).
Wisniewski, N. et. al., "Methods for reducing biosensor membrane biofouling," Colloids and Surfaces B: Biointerfaces, 18:197-219 (2000).
Woderer, S., "Continuous glucose monitoring in interstitial fluid using glucose oxidase-based sensor compared to established blood glucose measurement in rats," Anal Chim Acta., 581(1):7-12 (2007), Available online Aug. 18, 2006.
Office Action for Canadian Application No. 2,813,041, dated Nov. 26, 2015, 6 pages.
Office Action for Canadian Application No. 2,813,041, dated Jul. 15, 2016, 4 pages.
European Search Report for European Application No. 11831627.2, dated Feb. 23, 2017, 9 pages.
Notice of Reasons for Rejection for Japanese Application No. 2015-205520, dated Oct. 4, 2016, 8 pages.
Office Action for U.S. Appl. No. 14/461,144, dated Sep. 9, 2016, 10 pages.
Leavesley, S. J. et al., "Hyperspectral imaging microscopy for identification and quantitative analysis of fluorescently-labeled cells in highly autofluorescent tissue," J. Biophontonics, Jan. 2012;5(1):67-84. doi: 10.1002/jbio.201100066. Epub Oct. 11, 2011.
Shibata, H. et al., "Injectable hydrogel microbeads for fluorescence-based in vivo continuous glucose monitoring", Proceedings of the National Academy of Sciences of the United States of America, Oct. 19, 2010, vol. 107, No. 42, pp. 17894-17898.
Young et al., "A novel porous collagen scaffold around an implantable biosensor for improving biocompatibility. I. In vitro/in vivo stability of the scaffold and in vitro sensitivity of the glucose sensor with scaffold," Journal of Biomedical Materials Research Part A., 2008, vol. 87, pp. 136-146.
Office Action for Canadian Application No. 2,813,041, dated Jun. 6, 2017, 3 pages.
Patent Examination Report No. 1 for Australian Application No. 2015200893, dated Aug. 22, 2016, 5 pages.
Patent Examination Report No. 2 for Australian Application No. 2015200893, dated Mar. 1, 2017, 4 pages.
Notice on the First Office Action for Chinese Application No. 201510471187.8, dated Aug. 21, 2017, 25 pages.
Notice of Reasons for Rejection for Japanese Application No. 2015-205520, dated Sep. 5, 2017, 11 pages.
Office Action for U.S. Appl. No. 14/461,144, dated Jun. 16, 2017, 10 pages.
International Search Report and Written Opinion for International Application No. PCT/US2016/039566, dated Dec. 2, 2016, 9 pages.

\* cited by examiner

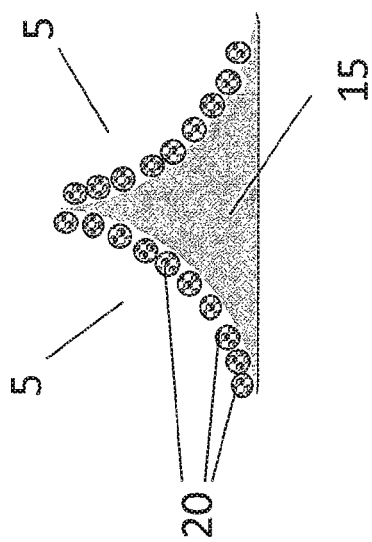
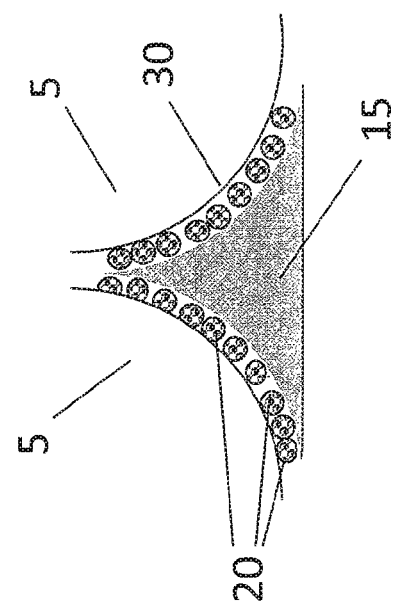

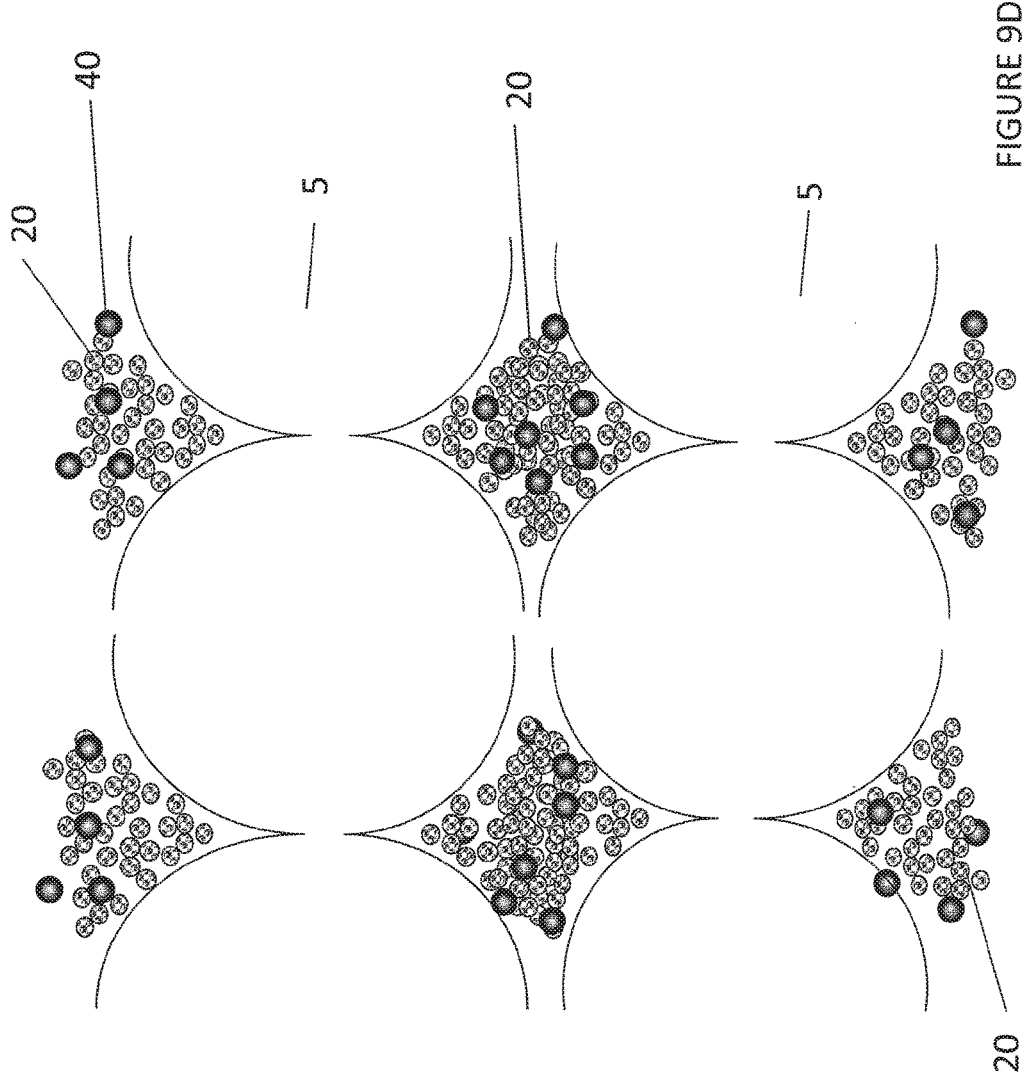

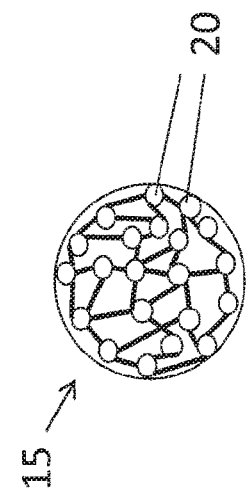
FIGURE 12
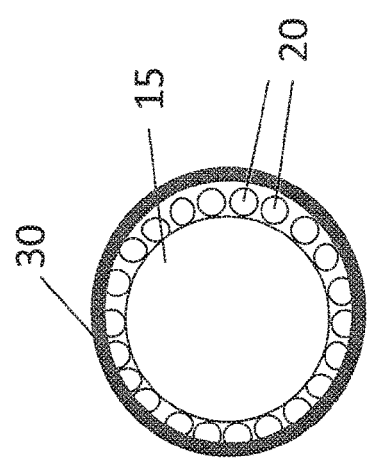
FIGURE 14
FIGURE 11
FIGURE 13

TISSUE-INTEGRATING SENSORS

CROSS-REFERENCE TO RELATED APPLICATIONS

The present application is a continuation of U.S. patent application Ser. No. 13/267,741, filed Oct. 6, 2011, which claims the benefit of U.S. Provisional Application No. 61/390,252, filed Oct. 6, 2010, each entitled "Tissue-Integrating Sensors," the disclosure of each of which is hereby incorporated by reference in its entirety.

TECHNICAL FIELD

The present disclosure is in the field of biosensors.

BACKGROUND

In the management of many conditions, the regular measurement of analytes in vivo is required. It has been a long-standing objective of both medical science and the military to implant sensors inside the human body that continuously and accurately determine changes in physiologic, metabolic, or fatigue status; measure the concentration of biothreat or therapeutic agents in vivo; and provide early detection of disease prior to the onset of symptoms. Doing so non-invasively with minimal user maintenance is essential, and sensor longevity of months to years is crucial in actual user environments.

For example, measurement of glucose in the blood is essential in order to ensure correct insulin dosing in diabetic patients. Furthermore, it has been demonstrated that in the long term care of the diabetic patient better control of the blood glucose levels can delay, if not prevent, the onset of retinopathy, circulatory problems and other degenerative diseases often associated with diabetes. Thus there is a need for reliable and accurate self-monitoring of blood glucose levels by diabetic patients.

Currently, blood glucose is monitored by diabetic patients with the use of commercially available calorimetric test strips or electrochemical biosensors (e.g. enzyme electrodes), both of which require the regular use of a lancet-type instrument to withdraw a suitable amount of blood each time a measurement is made. On average, the majority of diabetic patients would use such instruments to take a measurement of blood glucose twice a day. However, the US National Institutes of Health recently recommended that blood glucose testing should be carried out at least four times a day, a recommendation that has been endorsed by the American Diabetes Association. This increase in the frequency of blood glucose testing imposes a considerable burden on the diabetic patient, both in terms of financial cost and in terms of pain and discomfort, particularly in the long-term diabetic who has to make regular use of a lancet to draw blood from the fingertips. Thus, there is clearly a need for a better long-term glucose monitoring system that does not involve drawing blood from the patient.

Over the last several decades, many attempts have been made to develop implanted sensors that provide frequent or continuous monitoring. For example, U.S. Pat. No. 4,703,756 to Gough et al., filed May 6, 1986, describes a sensor module for implantation in the body to monitor glucose and oxygen levels. However, due to electrical failure, degradation of the analyte recognition element (typically an enzyme), component degradation and delamination, these sensors typically fail after a relatively short period of time (e.g., hours to days). Another major failure mode of in vivo sensors is not failure of the sensor itself, but rather changes in the tissue immediately adjacent to the sensor due to the implantation of the sensor. The tissue at the interface of the sensor changes in such a way that it is no longer representative of the overall body state or disease state or analyte of interest.

U.S. Pat. No. 7,228,159 describes a senor comprising a plurality of non-biodegradable sensing particles embedded in a biodegradable matrix for injection into the dermis. However, as the matrix degrades, the sensing particles are ingested by macrophages and removed from the implant site. Similarly, U.S. Pat. No. 6,671,527 describes a sensor which is injected into epidermis and is ejected over time due to the normal sloughing of skin. U.S. Patent Application No. 2009/0131773 describes a carbohydrate (e.g., glucose) sensor made up of at least two different variants of an appropriate competitive binding assay.

Nielsen et al. (2009) *J. Diabetes Science and Technology* 3(1):98-109, Billingsley et al. (2010) *Anal. Chem.* 82(9): 3707-3713 and McShane et al. (2000) *IEEE Engineering in Medicine and Biology Magazine* 19:36-45 describe implantation of analyte-sensing microspheres or nanospheres. These individual sensing particles are taken up by macrophages if they are too small, and can migrate through the tissue, which is not desirable for explanation and not desirable to have the fluorescent signal disperse in an uncontrolled way. If the sensing particles are too big to be taken up by macrophages, they undergo the typical foreign body response (FBR), which limits the proximity of capillaries with respect to the implant. As sensors become encapsulated by avascular tissue, they lose ability to accurately sense blood borne analytes and as they become engulfed by phagocytic cells (small particles), they lose contact with interstitial fluid, which is the compartment necessary to be sensed for components such as glucose. Therefore, current sensing technologies typically fail after only a short time in the body (e.g., 2-7 days for commercially available sensors).

Thus, there remains a clear need for sensing technologies that are tissue integrating to provide long-term (e.g., weeks, months or years) and accurate readings by remaining in contact with interstitial fluid (not the internal cellular environment) and remaining in close proximity to the vasculature so that the interstitial fluid surrounding the sensor is in constant rapid equilibrium with nearby capillaries.

SUMMARY

Disclosed herein are tissue-integrating sensors, systems comprising these sensors and methods of using these sensors and systems for the measurement of various analytes.

Currently, continuous analyte sensors for monitoring body chemistry (microdialysis, electrochemical, skin tattoo sensors, etc.) do not provide accurate, long-term data due to the progressively declining capillary density and/or foreign body response. The integration of capillaries into and throughout the sensor (sensing media) is a major improvement over what currently exists. The capillary enhancement gives rise to improved accuracy and reduced lag time.

In one aspect, provided herein are a tissue-integrating sensor for detecting an analyte, the sensor comprising a tissue-integrating scaffold; and one or more sensing moieties, wherein the sensing moieties produce a detectable signal in the presence of the analyte; and further wherein the sensor provides detection of the analyte when placed (e.g., implanted) into the tissue of a subject. The tissue-integrating sensors as described herein can provide long-term detection of the analyte(s). In certain embodiments, the tissue-integrating scaffold consists of the one or more sensing moieties (e.g., polymeric sensing moieties formed into a scaffold). The tissue-integrating sensors may comprise one or more polymers, for example one or more hydrogels. The sensing moieties may be embedded and/or attached to the exterior of the scaffold or may form the scaffold itself. In certain embodiments, the scaffold is porous and further wherein at least two of the pores are interconnected. In certain embodiments, the sensing moieties comprise microspheres or nanospheres. Any of the sensors described herein may include one or more layers (with sensing moieties in one or more of the layers) and/or one or more fibers.

Any of the sensors described herein may further comprise additional components, for example, a coating on the exterior of the sensor and/or one or more additional reference (calibration) moieties, for example for calibrating the signal detected from the sensing moieties.

In yet another aspect, provided herein is a system for detecting an analyte, the system comprising one or more of the tissue-integrating sensors as described herein; and an interrogator that generates (e.g., light that causes the sensing moieties to emit light) and/or measures the signal produced by the sensing moieties. In certain embodiments, the system further includes one or more of the following: a detector, a signal receiver, a signal transmitter, a signal processing component, an energy storage component, a data storage component, a data transmitter, a data display device, a data processing component and combinations thereof.

In yet another aspect, provided herein are methods of making and using the sensors and systems as described herein. In certain embodiments, provided herein is a method for detection of an analyte in a tissue of a subject, the method comprising integrating one or more sensors as described herein into the tissue and detecting the presence of the analyte.

BRIEF DESCRIPTION OF THE DRAWINGS

FIG. 2, panels A to E, depict a cross-sections of exemplary tissue integrating implants as described herein following implantation into a tissue and showing tissue in-growth into the pores following implantation into a subject.

FIG. 4 depicts a cross-section of a portion (boxed area of FIG. 1) of an exemplary tissue-integrating implant as described herein in which sensing moieties are attached to the surface of the solid scaffold portions.

FIG. 5 depicts a cross-section (boxed area of FIG. 1) of an exemplary tissue-integrating implant as shown in FIG. 4 and further including an exterior coating on or over the sensing moieties.

FIG. 10, panels A and B, are overviews of exemplary multi-layered cylindrical sensing media (tissue integrating sensor) as described herein.

FIG. 11 is a cross-section of an exemplary sensing media as shown in FIG. 9A.

FIG. 12 is a cross-section of an exemplary sensing media as shown in FIG. 9B.

FIG. 13 is a cross-section of an exemplary sensing media as shown in FIG. 12 and further including a coating exterior to the sensing moieties on the surface of the scaffold.

FIG. 14 is a cross-section of an entire (e.g., cylindrically shaped) or portion of (e.g., individual fiber) an exemplary sensing implant as described herein in which the scaffold is made from polymer where the polymer itself is composed of sensing moieties.

DETAILED DESCRIPTION

Figure 1:
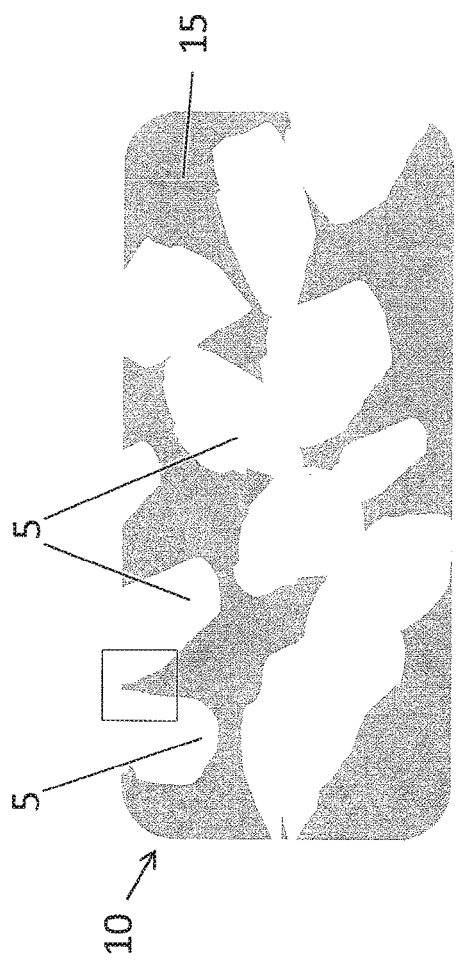
FIG. 1 depicts a cross-section of exemplary tissue-integrating implant as described herein showing the pores and solid scaffold portions.

Described herein are tissue-integrating sensors useful for accurate and optionally long term measurements of analytes in vivo. Also described herein are methods of using these sensors for optical detection of various biochemical analytes. Using reversible binding ligands and/or chemistries, the implantable sensors, systems and methods described herein provide for continuous or semi-continuous collection of data of various biochemical analytes, optionally without the use of implantable hardware of any type and/or enzymatic and electrochemical detection methods.

In particular, the tissue-integrating sensors that are the subject of this invention remain in good contact (close proximity) to blood vessels and have direct access to measurements of interstitial fluid. The tissue-integrating scaffold encourages capillary growth into and/or nearby the sensing media. The sensing media is devoid of electronics, making the sensing media seem less foreign to the body than implants that contain electronics. Additionally the tissue-integrating sensing media may have a modulus closer to the texture of tissue, thus enhancing the integration in the tissue.

Thus, unlike other devices, the sensors described herein allow capillaries to grow in close proximity to all regions of the sensor (e.g., on the surface and inside), which results in accurate analyte measurements, including over long term. Embedding, attaching or forming scaffolds out of nano-sized sensing elements results in tissue-integrating sensing media that allows in-growth, including of tissue and capillaries, in and/or around the sensors. Tissue integrating sensors minimize the foreign body response and/or promote vascularization. Capillary growth directly into and throughout the sensor allows unencumbered access to analytes of interest in the blood (e.g. glucose, lactate, pyruvate, cortisol, ions, proteins, nucleic acids, alcohols, urea, etc.). The level of tissue integration and proximity of capillaries to all regions of the sensor will provide a close, stable relationship between the analyte concentration in the blood and in the tissue surrounding the sensing media.

Advantages of the device and methods described herein include, but are not limited to: (1) providing devices that integrate into the subject (e.g., through tissue and/or capillary in-growth; (2) providing devices which can be implanted through syringe injection, meaning that no surgery is required to put the sensing media in place in the body; (3) providing devices that do not include sensor electronics in the body; (4) providing devices comprising material(s) having properties more similar to actual tissue (e.g., modulus that is more similar to tissue's modulus and hydrogel water content) to allow a better acceptance into the tissue; (5) providing devices that accurately assess analyte(s) for long periods of time (e.g., greater than a week, typically weeks, months or years) and/or (6) providing devices of small dimensions which will give result in increased patent comfort and better acceptance by the body.

It must be noted that, as used in this specification and the appended claims, the singular forms "a", "an", and "the" include plural referents unless the content clearly dictates otherwise. Thus, for example, reference to a sensor comprising "a sensing moiety" includes devices comprising of two or more sensing moieties. Likewise, reference to "an analyte" refers to two or more analytes.

Definitions

The term "tissue integrating" refers to a material (e.g., scaffold) which, when integrated into living tissue remains in close proximity with the blood vessels of the tissue (e.g., capillaries). By "close proximity," is meant that the average distance from any point within the material (scaffold) implanted into the tissue to the nearest blood vessel is no greater than 100 microns more than the average distance from any point in the native (original) tissue to the nearest blood vessel.

By "long-term" is meant that the implant senses the analyte for greater than about 7 days, for example weeks, months, or years.

By "biodegradable" or "bioabsorbable" is meant that the material is capable of being broken down by the subject's body over a period of time, ranging from days to weeks to months or years.

By "water-soluble" is meant that the molecules of the material are capable of dissolving in water. Thus, biodegradable materials may include water-soluble biomaterials.

By "hydrogel" is meant a material that absorbs a solvent (e.g. water), undergoes rapid swelling without discernible dissolution, and maintains three-dimensional networks capable of reversible deformation.

Sensing Media

Described herein are sensors (or sensing media) for implantation in a subject. The sensors are made up of tissue-integrating scaffolds and at least one sensing moiety.

A. Tissue Integrating Scaffolds

The sensors described herein typically comprise a tissue-integrating scaffold (also referred to as a matrix) material. Preferably, the tissue-integrating scaffold of the invention may be constructed with materials and/or micro-architecture such that the scaffold promotes tissue-integration and/or vascularization. For example, porous scaffolds provide tissue biomaterial anchoring and promote in-growth throughout the pores. The resulting "hallway" or "channel" pattern of tissue growth are healthy, space-filling masses that persist over time and promote host cell integration. Most or all of the pores of the biomaterials described herein are preferably interconnected (co-continuous). The co-continuous pore structure of the biomaterials promotes space-filling in-growth of cells in the implant, which in turn limits the foreign body response and leads to long-term (greater than one week and up to years) persistence of the implant's ability to act as a sensor. Alternative structures that provide tissue integrating scaffolds include fibers (e.g., 1 to 10 or more microns in diameter, such as 5, 6, 7, 8, 9, 10 or more microns), which may be arranged in non-random or random configuration. Tissue-integrating scaffolds (in any configuration) can also be formed by multiphoton polymerization techniques. Kaehr et al. (2008) *Proc. Nat'l. Acad. Sci. USA* 105(26):8850-8854; Nielson et al. (2009) *Small* 1:120-125; Kasprzak, Doctoral Dissertation, Georgia Institute of Technology, May 2009.

The tissue-integrating scaffold of the invention may comprise any material, including but not limited to synthetic polymers, naturally-occurring substances, or mixtures thereof. Exemplary synthetic polymers include, but are not limited to polyethylene glycol (PEG), 2-hydroxyethyl methacrylate (HEMA), silicone rubber, poly([epsilon]-caprolactone) dimethylacrylate, polysulfone, (poly)methy methacrylate (PMMA), soluble Teflon-AF, (poly)ethylenetetrapthalate (PET, Dacron), Nylon, polyvinyl alcohol, polyacrylamide, polyurethane, and mixtures thereof. Exemplary naturally-occurring materials include, but are not limited to, fibrous or globular proteins, complex carbohydrates, glycosaminoglycans, extracellular matrix, or mixtures thereof. Thus, the polymer scaffold may include collagens of all types, elastin, hyaluronic acid, alginic acid, desmin, versican, matricelluar proteins such as SPARC (osteonectin), osteopontin, thrombospondin 1 and 2, fibrin, fibronectin, vitronectin, albumin, chitosan etc. Natural polymers may be used as the scaffold or as an additive.

In certain embodiments, the tissue-integrating scaffold comprises a hydrogel. For example, the polymer scaffold may comprise a hydrogel, for example by reacting hydroxyethyl methacrylate (HEMA), poly (hydroxyethyl methacrylate), pHEMA. Furthermore, various comonomers can be used in combination to alter the hydrophilicity, mechanical and swelling properties of the hydrogel (e.g. PEG, NVP, MAA). Non-limiting examples of polymers include 2-Hydroxyethyl methacrylate, polyacrylamide, N-vinylpyrrolidone, N,N-Dimethylacrylamide, poly(ethylene glycol) monomethacrylate (of varying molecular weights), diethylene glycol methacrylate, N-(2-hydroxypropyl)methacrylamide, glycerol monomethacrylate, 2,3-dihydroxypropyl methacrylate and combinations thereof. Non-limiting examples of cross-linkers include tetraethylene glycol dimethacrylate, poly(ethylene glycol) (n) diacrylate (ofvarying molecular weights), ethoxylated trimethylolpropane triacrylate, bisacrylamide and combinations thereof. Non-limiting examples of initiators include irgacure Series (UV), Azobisisobutyronitrile (AIBN) (thermal), Ammonium Persulfate (APS) (thermal).

The tissue-integrating scaffold may be a sphere-templated hydrogel, for instance an inverse colloid crystal, for example as described in U.S. Patent Publication No. 2008/0075752 to Ratner, et al. or other tissue integrating materials.

The scaffold may be degradable, either by the body (biodegradable) or by the application of an external initiator to start or speed up the degradation process (e.g. UV, ultrasonics, radio frequency, or other exogenous sources to initiate degradation.). For example, the tissue-integrating scaffold may be comprised of any biodegradable or bioresorbable polymers, including but not limited to degradable forms of alginates, poly(lactic acid), poly(vinyl alcohol), polyanhydrides, poly(glycolic acid), microporous polyesters, microporous polyethers and cross-linked collagen. One specific example is UV-photopolymerization of poly(ethylene glycol)-diacrylate and acrylated protease-degradable peptides and VEGF as described by Phelps, et al (2010) *Proc. Nat'l. Acad. Sci. USA* 107(8):3323-3328.

Other specific examples are polymers described by Kloxin et al (2009) *Science* 324:59-63 and U.S. Pat. No. 6,013,122 whose degradation is controlled through exposure to exogenous energy forms as well as Alexeev et al. (2003) *Anal. Chem.* 75:2316-2323; Badylak et al. (2008) *Seminars in Immunology* 20:109-116; Bridges et al. (2010) 94(1):252-258; Isenhath et al. (2007) *Research* 83A:915-922; Marshall et al. (2004) *Polymer Preprints, American Chemical Society, Division of Polymer Chemistry* 45:100-101; Phelps et al. (2010) *Proc. Nat'l. Acad. Sci. USA.* 107(8):3323-8; Ostendorf and Chichkov (2006) *Two Photon Polymerization: A New Approach to MicroMachining, Photonics Spectra;* Ozdemir al. (2005) *Experimental and Clinical Research, Plast. Reconstr. Surg.* 115:183; U.S. Patent Publication No. 20080075752; Sanders et al. (2003) *Journal of Biomedical Materials Research* Part A 67A(4):1181-1187; Sanders et al. (2002) *Journal of Biomedical Materials Research* 62(2): 222-227; Sanders et al. (2003) *Journal of Biomedical Materials Research* 65(4):462-467; Sanders et al. (2005) Biomaterials 26:813-818; Sanders et al. (2005) *Journal of Biomedical Materials Research* Part A 72(3):335-342; Sanders (2003) *Journal of Biomedical Materials Research* 67(4): 1412-1416; Sanders et al. (2000) *Journal of Biomedical Materials Research* 52(1):231-237; and Young Min Ju et al. (2008) *J Biomed Mater Res* 87A:136-146.

In certain embodiments, the tissue-integrating scaffold of the invention is constructed such that tissue response modifiers are released from the scaffold material to promote or enhance tissue-integration and vascularization.

In addition, the tissue-integrating scaffold of the invention may be constructed such that it has conduits, pores or pockets that are hollow or filled with degradable, angiogenic, or other substances (e.g. stem cells). As noted above, once in the body, the biodegradation of the material filling the conduits, pores or pockets, creates space for tissue, including capillaries to integrate with the material. The degradable material that initially fills the conduits, pores or pockets may enhance vessel growth or tissue growth within the scaffold. This architecture promotes new vessel formation and maintains healthy viable tissue within and around the implant.

The tissue-integrating scaffold of the invention may be constructed such that it is permeable to analytes of interest (e.g. glucose can diffuse into a tissue-integrating hydrogel scaffold and reach the sensing moieties that are embedded within the hydrogel matrix).

FIG. 1 depicts an exemplary embodiment of a porous tissue-integrating implants described herein. The device as a whole is generally designated 10 and is shown in cross-section in a three-dimensional block. FIG. 1 shows an embodiment in which all of the pores 5 are interconnected. The pores 5 are within the solid scaffold portions 15.

Figure 2A:
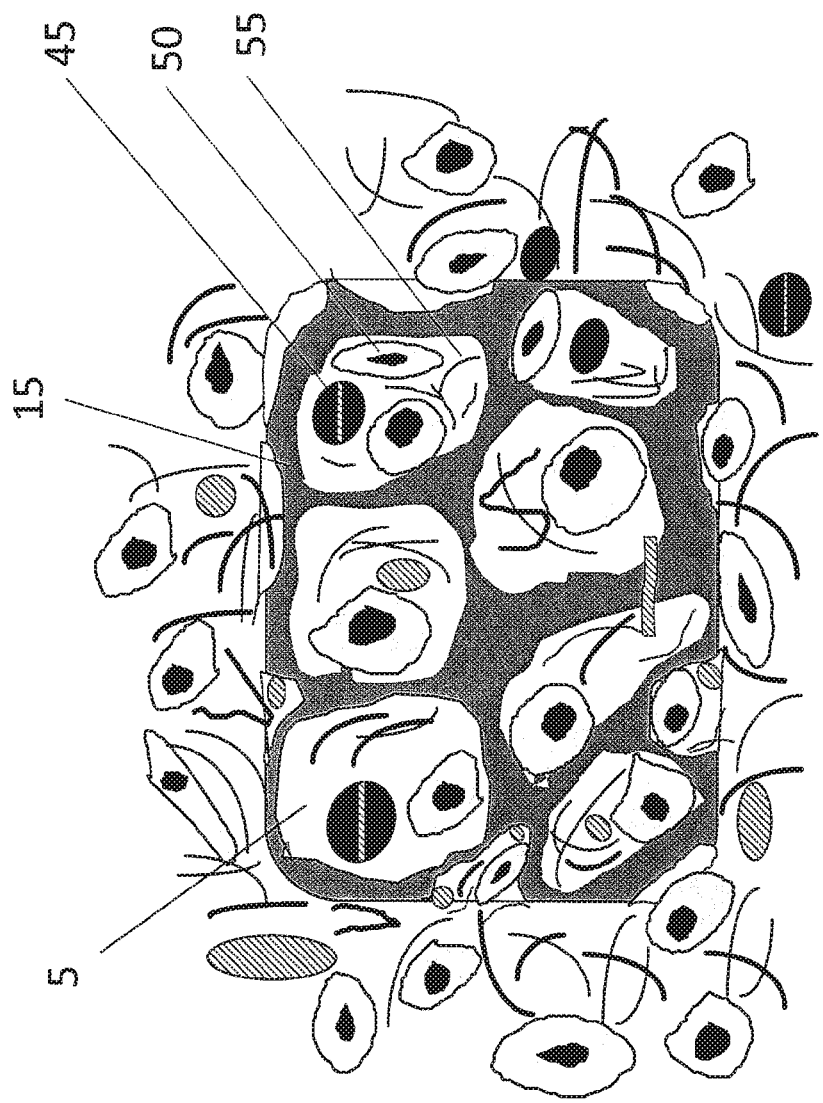
FIG. 2A is a schematic cross-section of a portion (boxed area) of the device shown in FIG. 1.
Figure 2C:
FIGS. 2B and 2C are reproductions of histology photographs showing a cross-section of tissue including the implanted sensor 1 week (FIG. 2B) or one more (FIG. 2C) after implantation of a sensor as described herein.
Figure 2B:
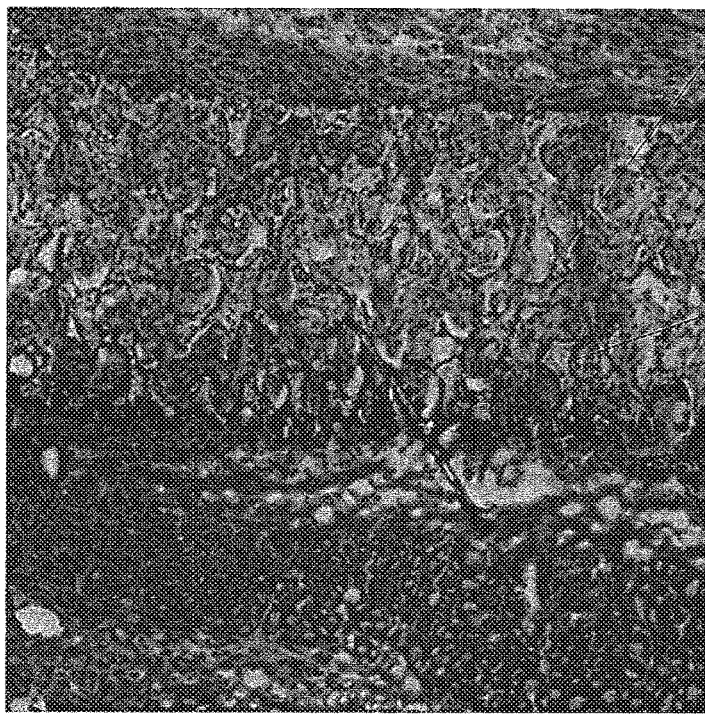
Figure 2D:
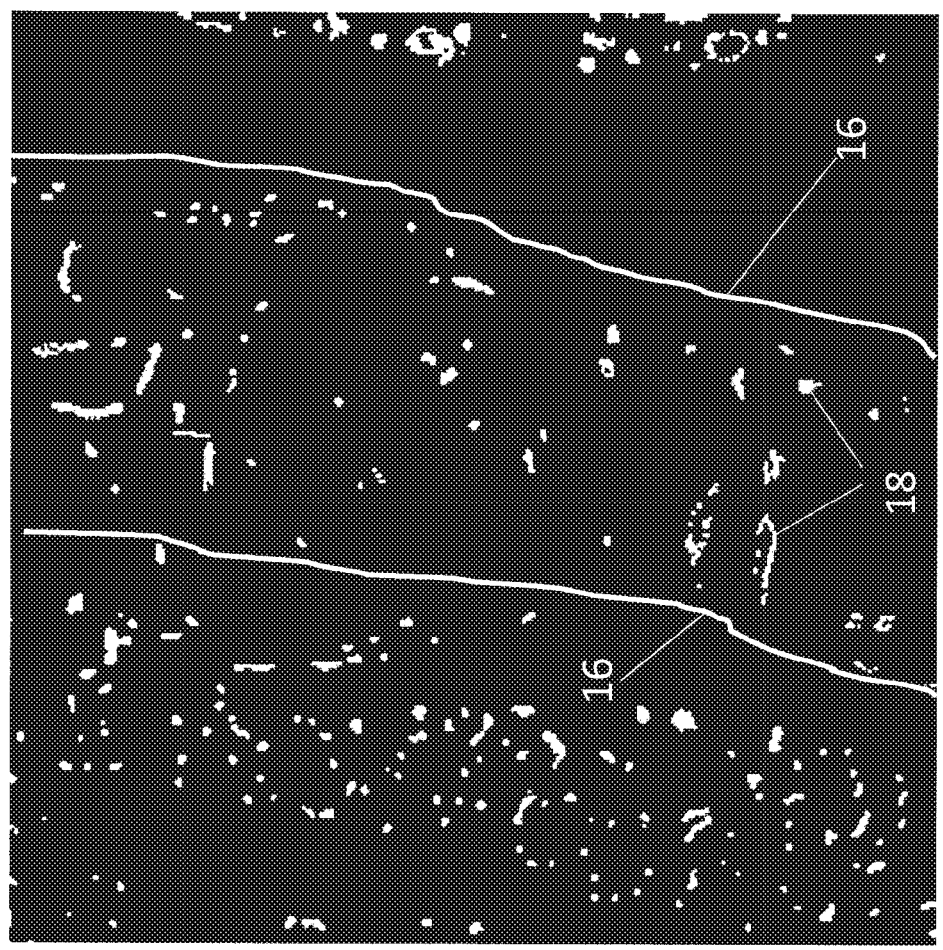
FIGS. 2D and 2E are reproductions of immunohistochemistry photographs (staining for capillaries for CD31) showing a cross-section of tissue including the implanted sensor 1 week (FIG. 2D) and 1 month (FIG. 2E) post-implantation of the sensor.
Figure 2E:
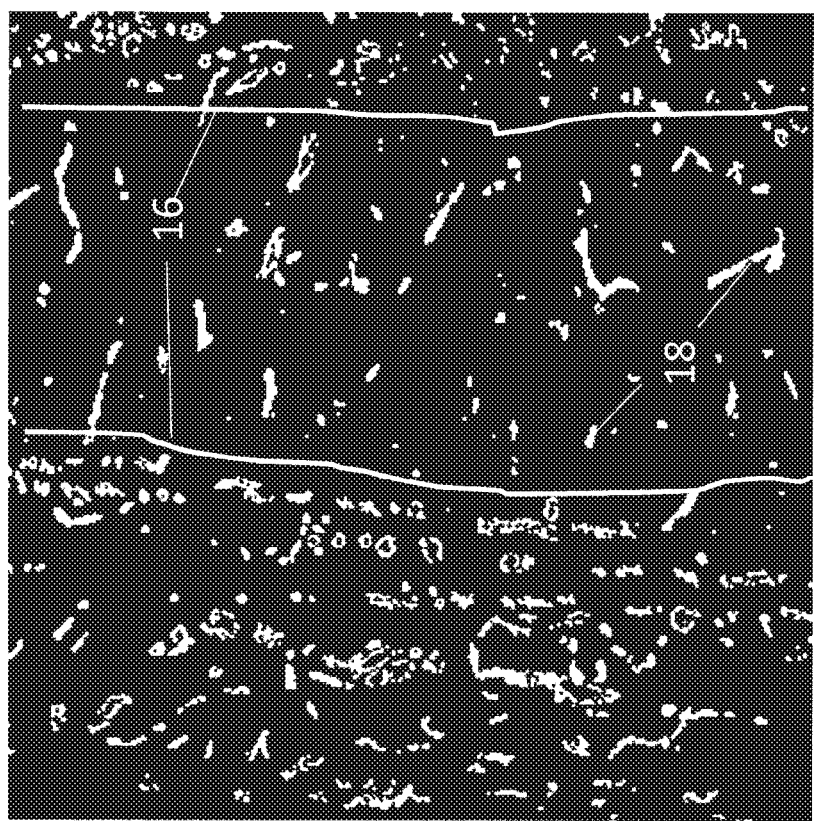

FIG. 2A depicts an exemplary embodiment of a porous tissue-integrating implant as described herein following implantation and tissue in-growth. The scaffold 15 is shown following growth of blood vessels 45, cells 50 and extracellular matrix material 55 (e.g., collagen) in and around the implant after implantation. FIGS. 2B and 2C show histology photographs of tissue (rat skin) including an integrated implant 15 as described herein. FIG. 2B shows the implant in the tissue 1 week following implantation and FIG. 2C shows the implant 1 month following implantation into Sprague-Dawley rats. As shown, the tissue 19 grows into the implant, keeping the implant in close proximity to the blood vessels of the tissue and without a significant foreign body response. FIGS. 2D and 2E are reproductions of photographs showing immunohistochemistry staining for vasculature (using CD31 antibodies) 1 week (FIG. 2D) and 1 month (FIG. 2E) following implantation into skin (subcutaneous) of Sprague-Dawley rats. The approximate boundaries of the scaffold 16 are shown as well as capillary ingrowth 18 into the implanted scaffold.

Figure 6:
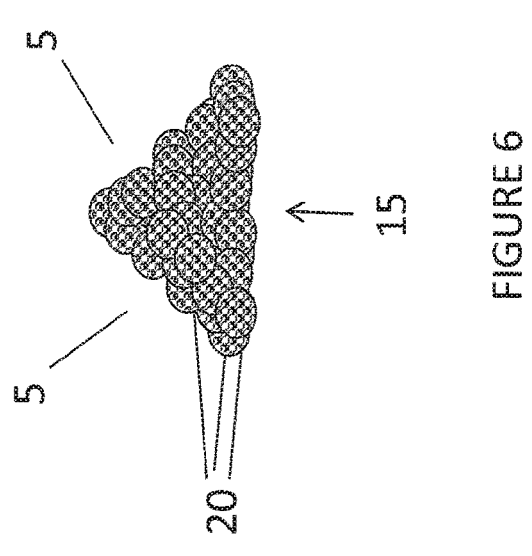
FIG. 6 depicts a cross-section (boxed area of FIG. 1) of an exemplary tissue-integrating implant as described herein in which solid scaffold portions are made from sending moieties in the form of particles bonded together.

In certain embodiments, the tissue-integrating scaffold is made up solely or primarily of sensing moieties (see, e.g., FIGS. 5 and 6). For example, sensing particles can be bonded together using any suitable method (chemical, adhesive, thermal, etc.). In certain embodiments, the sensing particles comprise a polymer, for example PEG-coated particles (e.g., microspheres). In other embodiments, the scaffold comprises a polymer that itself is composed of sensing moieties. See, FIG. 6.

The tissue integrating implant can be of any suitable form, including, but not limited to block-like (or any thickness), cube-like, disk-shaped, cylindrical, oval, round, random or non-random configurations of fibers and the like. In certain embodiments, the sensor comprises one or more fibers, which may be organized in a non-random fashion (e.g., grid, layered grid, etc., see, FIG. 9E) or in a random fashion (see, e.g., FIG. 9F).

B. Sensing Moieties

The tissue-integrating scaffolds described herein are typically combined with (or made up of) sensing moieties that detect one or more analytes.

Non-limiting examples of analytes that may be detected by the sensing moieties include oxygen, reactive oxygen species, glucose, lactate, pyruvate, cortisol, creatinine, urea, sodium, magnesium, calcium, potassium, vasopressin, hormones (e.g., Luteinizing hormone), pH, cytokines, chemokines, eicosanoids, insulin, leptins, small molecule drugs, ethanol, myoglobin, nucleic acids (RNAs, DNAs), fragments, polypeptides, single amino acids and the like.

Any suitable moiety can be used to sense the analyte of interest, including not limited to analyte binding molecules (e.g. glucose binding proteins), competitive binding molecules (e.g. phenylboronic acid based chemistries), analyte specific enzymes (e.g. glucose oxidase), ion sensitive materials, or other analyte sensitive molecules (e.g. oxygen sensitive dyes such as porphyrins). The sensing moieties may be in any form, for example, microspheres, nanospheres, fibers, etc. A single implant (tissue-integrating scaffold) typically includes a plurality of sensing moieties. In certain embodiments, the sensing moieties are all the same while in other embodiments, a mixture of two or more sensing moieties is used.

To enhance or create a detectable signal, sensing molecules may be labeled with a reporter (e.g., one or more fluorophores, one or more gold particles, one or more quantum dots and/or one or more single-walled carbon nanotubes). Sensing molecules may also create a signal through swelling, optical diffraction, change in absorbance FRET, quenching.

Non-limiting examples of suitable sensing molecules include but are not limited to dye labeled Concanavalin A with glycodendrimer or dextran (see, e.g., Ballerstedt et al. (1997) *Anal. Chim. Acta* 345:203-212) and alcohol sensitive oxo-bacteriochlorin derivative fluorescent binding protein developed by Takano, et al (2010) *The Analyst* 135:2334-2339 as well as Vladimir et al. (2004) *Clinical Chemistry* 50:2353-2360; Aslan et al. (2005) Chem. 1; 77(7):2007-14; Ballerstadt et al. (1997) *Anal. Chem. Acta* 345:203-212 (1997); Billingsley et al. (2010) *Anal. Chem* 82(9):3707-3713; Brasuel et al. (2001) *Anal. Chem* 73(10):2221-2228; Brasuel, et al. (2003) *The Analyst* 128(10):1262-1267; Horgan et al. (2006) *Biosensors and Bioelectronics* 211838-1845; Ibey et al. (2005) *Anal Chem* 77:7039-7046; Nielsen et al. (2009) *Journal of Diabetes Science and Technology* 3(1):98-109; McShane et al. (2000) *IEEE Engineering in Medicine and Biology Magazine* 19:36-45; Mansouri & Schultz (1984) *Bio/Technology* 23:885-890; Rounds, et al. (2007) *Journal of Fluorescence* 17(1):57-63; Russell et al. (1999) *Analytical Chemistry* 71(15):3126-3132; Schultz et al. (1982) *Diabetes Care* 5:245-253; Srivastava, & McShane (2005) *Journal of Microencapsulation* 22(4):397-411; Srivastava et al. (2005) *Biotechnology and Bioengineering* 91(1): 124-131; Takano et al. (2010) *The Analyst* 135:2334-2339.

The sensing moiety element may comprise other molecules besides sensing molecules, such as carrier molecules/polymers (e.g. the sensing moiety element may comprise PEG nanospheres, alginate particles or other carrier materials that contain sensing molecules). The sensing moiety element may also contain reference molecules or stabilizing molecules that do not sense any analytes, but that serves as calibrators (e.g., a reference dye or any substance that provides a reference signal to which the signal modulated by the analyte of interest may be compared for calibration) or stabilizer (e.g. catalayse, any free-radical scavenger which helps preserve the sensing moieties or other stabilizer).

The sensing moiety element may be thermally responsive material, pressure-responsive material or materials that swell, shrink, change optical properties, or change other measurable properties in response to a stimulus.

C. Sensing Media

The combination of the tissue-integrating scaffold with the analyte sensing moieties may be termed implantable sensing media, sensing media, tissue integrating sensor, tissue-integrating biosensor, tissue-integrating sensing media or variations thereof.

The analyte sensing moieties may be combined with the tissue-integrating scaffolds in a variety of ways to produce tissue-integrating sensors. In some embodiments the sensing moieties are physically entrapped or chemically bound within the scaffold. In other embodiments, the sensing moieties are attached directly (e.g., via covalent or noncovalent linkages) to the surface of the tissue-integrating scaffold and may optionally be covered by an exterior coating. The purpose of the exterior coating is described as, but not limited to the following: to hold the sensing moieties in place, to protect the sensing moieties from external forces, to limit/impede diffusion of various molecules and/or to provide a desired exterior surface, and to conduct or transduce the sensing signal from the chemistry to the scaffold and/or external detector.

In some embodiments the tissue-integrating scaffold itself is composed of sensing moieties where the sensing moieties are in the form of particles (spherical or other shapes) that are bonded together (e.g. chemically, thermally, pressure, etc.) or where the polymer itself provides the sensing capability (e.g. stimuli-sensitive polymers).

In another embodiment, the tissue integrating scaffold is composed of distinct layers where sensing moieties are physically entrapped or chemically bound to or within specific layers of the scaffold, and other layers provide other features such as mechanical strength, elasticity, conductivity or other properties.

In another embodiment, the tissue-integrating scaffold is composed of a polymer that swells or shrinks in response to a stimulus (e.g. concentration of an analyte of interest, temperature, or other stimuli). The shrinking or swelling may cause optical change (e.g. due to light diffraction, change in distances between gold nanoparticles contained within the matrix, or other interaction (Aleexev et al and Asian, et al)).

Table 1 below provides a matrix showing how sensing moieties can be combined with tissue-integrating scaffolds in a variety of ways to tissue-integrating sensing media.

dyes, fluorescent particles, lanthanides, nanoparticles, microspheres, quantum dots or other additives or elements of the implant whose signal does not change due to the presences of the analyte (e.g., glucose). See, e.g., Chaudhary et al. (2009) *Biotechnology and Bioengineering* 104(6): 1075-1085. Fluctuations in the reference (calibration) signal(s) can be used to correct or calibrate the sensing

TABLE 1

Sensing Media/Scaffold Matrix

| | Sensing Moieties | | | |
|---|---|---|---|---|
| Tissue-integrating Scaffolds | Sensing particles (e.g. PEG microspheres containing ConA with glycodendrimer, alginate nanospheres containing ApoGox with reported dye.) | Sensing chemistry (e.g. boronic acid based chemistry, sensing chemistry attached to quantum dots or gold nano-rods) | Any other fluorescent sensing assay (e.g. glucose oxidase with porphyrin dye) | Stimuli responsive moieties (temperature, pressure, other) |
| Permeable Biomaterial Scaffold (e.g. hydrogel ICC) (Kotov, Marshall) | Polymerization (SM contained within mesh of scaffold polymer) Immobilization (conjugation or physical entrapment) of SM on surface Making scaffold of sensing moiety | Polymerization (SM contained within mesh of scaffold polymer) Immobilization (conjugation or physical entrapment) of SM on surface Making scaffold of sensing moiety | Polymerization (SM contained within mesh of scaffold polymer) Immobilization (conjugation or physical entrapment) of SM on surface Making scaffold of sensing moiety | Polymerization (SM contained within mesh of scaffold polymer) Immobilization (conjugation or physical entrapment) of SM on surface Making scaffold of sensing moiety |
| Non-Permeable Scaffold (ICC) (e.g. Porex, MedPor) | Immobilization of SM on surface Physical entrapment of SM on surface | Immobilization of SM on surface Physical entrapment of SM on surface | Immobilization Of SM on surface Physical entrapment of SM on surface | Immobilization Of SM on surface Physical entrapment of SM on surface |
| Naturally derived scaffolds (e.g. fibrin, BSA, collagen synthetic or decellularized ECM (sECM), Prestwich, Badylak, Taylor, | SM contained within mesh of naturally derived matrix Immobilization of SM on surface Physical entrapment of SM on surface | SM contained within mesh of naturally derived matrix Immobilization of SM on surface Physical entrapment of SM on surface | SM contained within mesh of naturally derived matrix Immobilization of SM on surface Physical entrapment of SM on surface | SM contained within mesh of naturally derived matrix Immobilization of SM on surface Physical entrapment of SM on surface |
| Small fibers (Sanders) | Polymerization (SM trapped IN fiber matrix) Immobilization (conjugation or physical entrapment) of SM on surface Making scaffold of sensing moiety Multi-layer fibers (e.g. sensing layer, biocompatibility layer, stabilizing or structural layer, voids or cellular conduits | Polymerization (SM trapped IN fiber matrix) Immobilization (conjugation or physical entrapment) of SM on surface Making scaffold of sensing moiety Multi-layer fibers (e.g. sensing layer, biocompatibility layer, stabilizing or structural layer, voids or cellular conduits | Polymerization (SM trapped IN fiber matrix) Immobilization (conjugation or physical entrapment) of SM on surface Making scaffold of sensing moiety Multi-layer fibers (e.g. sensing layer, biocompatibility layer, stabilizing or structural layer, voids or cellular conduits | Polymerization (SM trapped IN fiber matrix) Immobilization (conjugation or physical entrapment) of SM on surface Making scaffold of sensing moiety Multi-layer fibers (e.g. sensing layer, biocompatibility layer, stabilizing or structural layer, voids or cellular conduits |

In certain embodiments, the implant (sensing media) further comprises additional moieties (e.g., non-sensing or additional sensing moieties different from the sensing moieties), for example reference (or calibration) moieties. Reference or calibration moieties include, but are not limited to, signal(s). Reference signals might fluctuate due to changes in the amount of light reaching the implant (ambient light changes, fluctuating LED or laser source). Sensing signals would also be subject to fluctuations in the amount of light reaching the implant; however it is desirable that the signal of interest only fluctuates based on analyte (e.g., glucose) fluctuations. Therefore the reference signal is used to correct or calibrate the sensing signal when it fluctuates due to influences other than changes in glucose concentration. Reference signals might also fluctuate due to changes in the reference moiety itself (e.g. photodegratation, chemical degradation). The sensing signal(s) would have the same degradation or a rate of degradation that is relatable to the reference to allow for correction or calibration by the reference. Reference signals might also fluctuate due to physiological fluctuations that alter the light propagation through tissue (e.g. dehydration, oxygenation, blood flow). Sensing signals would be affected in the same way or in a way that is relatable to the reference fluctuations thereby permitting correction or calibration of the sensing signal by the one or more references. Thus, the sensing signal can be calibrated by reference to the signal(s) obtained from the calibration (reference) moieties.

In certain embodiments, the sensing moieties detect glucose and the reference moiety comprises a molecule that measures (produces a detectable signal in the presence of) oxygen ($O_2$). As noted above, the sensing moieties can comprise an enzyme, for example glucose oxidase which is specific for the substrate glucose. The reaction of glucose oxidase causes the substrate glucose to be converted to D-glucono-1,5-lactone, which then hydrolyzes to gluconic acid. Oxygen is consumed and converted to $H_2O_2$. The reduction of $O_2$ in the vicinity of the enzyme can be measured by using an $O_2$-sensitive fluorescent dye, such as a porphyrin dye. These dye molecules are quenched in the presence of $O_2$, so the reduction of $O_2$ by the action of GOx, causes an increase in fluorescence. The amount of fluorescence emitted from the $O_2$ calibration moieties is thus proportional to the concentration of glucose in the sensor.

The concentration of $O_2$ in the tissue can also vary physiologically, thereby changing or limiting the reaction of the enzyme in the sensing moieties. Therefore, the $O_2$ concentration in the sensor can be measured independent of the glucose concentration. Such a reference measurement of $O_2$ would allow corrections to be made to the glucose-specific signal from the sensing moieties.

In another embodiment, an analyte-specific enzyme that causes a change in pH would require the use of a separate pH-sensitive fluorescent dye with an emission spectral peak different and distinguishable from the analyte-specific dye reporting on the activity of the analyte-specific enzyme, for example when the sensing moieties comprise, urease used for measuring urea.

In still further embodiments, the sensing moieties comprise a first fluorescent dye and the reference molecule comprises a second (different) fluorescent dye. As noted above, the sensing moieties may utilize an analyte-specific chemistry that includes a ligand receptor moiety and an analyte analogue moiety. One of the binding members is labeled with a fluorescent dye and the other binding member is labeled with a dye that quenches the fluorescent dye when the analyte analogue moiety binds to the ligand receptor moiety. Non-limiting examples include glycodendrimer, which binds to Concanavalin A, wherein the Concanavalin A is labeled with Alexafluor 647 and the glycodendrimer is labeled with QDY21 dark quencher. Concanavalin A binds to glucose and the glycodendrimer competes with glucose for the binding to Concanavalin A. The chemistry is immobilized as described in this invention within the tissue-integrating scaffold and implanted into the dermis or subcutaneous tissue. To measure glucose in the tissue, the tissue-integrating scaffold is illuminated from a patch reader on top of the skin above the implant with 650 nm light at desired intervals over the long-term life of the implant (e.g., every 5-60 minutes over a period of 90 days or more). The amount of fluorescent signal (e.g., from a molecule such as Alexafluor 647) detected is proportional to the concentration of glucose in the tissue. However, over the long-term life of the implants described herein, the dye can photobleach, i.e., the amount of fluorescent signal emitted back through the skin at a given glucose concentration is diminished. Thus, a reduction of fluorescence due to photobleaching can make it appear that analyte is at a lower concentration than it really is.

To correct for this effect, a separate internal photobleaching control is employed. In certain embodiments, the separate internal control is a second fluorescent dye, different from the fluorescent molecule included in the sensing moieties (e.g., Alexafluor 750 in the reference moieties when the sensing moieties comprise Alexafluor 647), which included immobilized in the scaffold. The fluorescence of reference moieties is not affected by the concentration of glucose, and both the first (e.g., Alexafluor 647) and second (e.g., Alexafluor 750) fluorescent dyes have predictable and well-characterized photobleaching rates. To control for the photobleaching of the dye of the sensing moieties, the fluorescence is measured for both dyes. The fluorescence value of the dye in the reference moieties can then be used to correct for any photobleaching of the dye in the sensing moieties.

In another embodiment, internal reference control materials can be employed that facilitate correcting for tissue optical variation. The tissue-integrating implanted biosensor typically resides 3-4 mm under the surface of the scan. It is well known that in skin excitation light and emitted fluorescent light in the near infrared range are highly scattered as the light traverses the tissue between the reader patch and the implant. The extent of absorption and scattering is affected by physical properties such as temperature or by tissue composition, including but not limited to variations in blood perfusion, hydration, and melanin concentration. Skin variations can occur between users or between different time points for a single patient, and these variations can affect the fluorescence excitation and emissions signals causing in accurate signals for the analyte-specific signal. Accordingly, a separate fluorescence molecule with emission spectra distinguishable from the analyte-specific fluorescence can be immobilized into the scaffold. The fluorescence from the molecule can be measured separately from the analyte-specific fluorescence to measure a signal that informs about variations in tissue composition. The dye selected is based on having a similar response to tissue variations as the analyte-specific dye. Dyes such as Alexafluor 750, various quantum dots (QD's), or lanthanide dye nanocrystals all can provide this capability.

Figure 3:
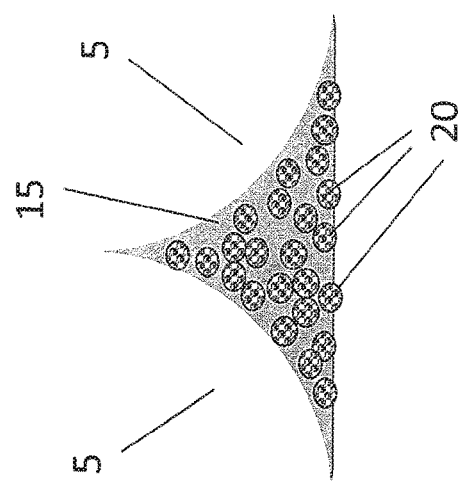
FIG. 3 depicts a cross-section (boxed area of FIG. 1) of an exemplary tissue-integrating implant (also known as the sensing media) as described herein in which sensing moieties are embedded (physically entrapped or chemically bound) within the solid scaffold portions.

FIGS. 3 to 8 depict cross-sections of exemplary tissue integrating implants as described herein. In each Figure, only a portion of the implant is depicted (e.g., boxed area of FIG. 1) and the pore 5 is depicted as a void. In particular, FIG. 3 depicts a cross-section of an exemplary tissue-integrating implant as described herein in which sensing moieties 20 are embedded within the solid scaffold portions 15. The sensing moieties 20 may be physically entrapped and/or chemically bound within the solid scaffold portions 15.

FIG. 4 depicts a cross-section of an exemplary tissue-integrating implant as described herein in which sensing moieties 20 are attached to the surface of the solid scaffold portions 15 (sensing moieties are within pores 5). FIG. 5 depicts the exemplary embodiment shown in FIG. 4 and further comprising an exterior coating 30 surrounding the sensing moieties.

Figure 7:
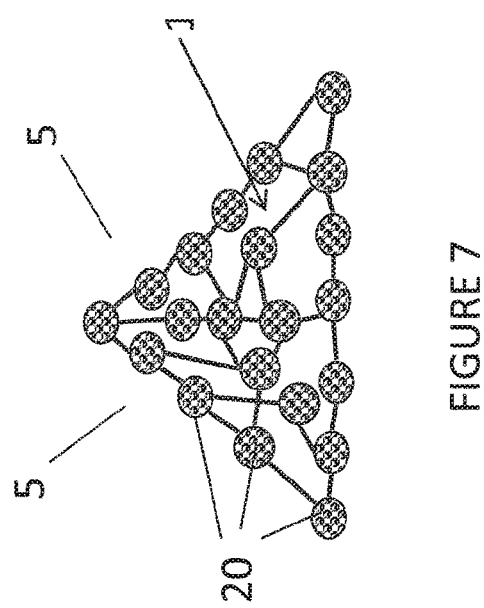
FIG. 7 depicts a cross-section (boxed area of FIG. 1) of an exemplary tissue-integrating implant as described herein in which solid scaffold portions are made from a polymer in which the polymer is composed of sensing materials.

FIG. 6 depicts a cross-section of an exemplary tissue-integrating implant as described herein in which solid scaffold portions 15 are made from sensing moieties 20 in the form of particles bonded together. FIG. 7 depicts a cross-section of a solid scaffold portion 15 made from a polymer in which the polymer is composed of sensing materials.

Figure 8:
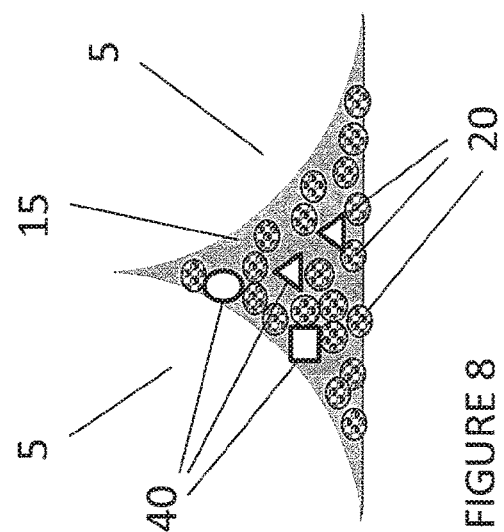
FIG. 8 depicts a cross-section of an exemplary tissue-integrating implant as shown in FIG. 3 and further including additional moieties (e.g., reference particle for calibration) embedded in the scaffold.

FIG. 8 depicts a cross-section of an exemplary tissue-integrating implant as shown in FIG. 3 and further including additional moieties 40 embedded in the solid portion 15 of the scaffold. The additional moieties 40 can be, for example, reference particles for calibration, including but not limited to particles that provide a stable signal (e.g., optical, magnetic, electrochemical, electrical, temperature, pressure, ultrasound, acoustic, radiation) to which the analyte sensing signals may be compared for calibration purposes. As shown, one or more different types of additional (reference) moieties can be used.

Figure 9B:
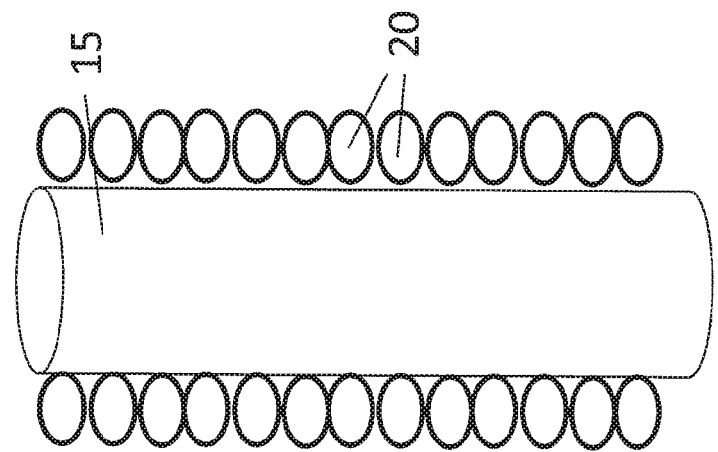
FIG. 9, panels A and F, are overviews and cross-sections of exemplary sensors as described herein.
FIG. 9A shows an exemplary single-layered (e.g., single layer fibers) cylindrical sensing media (tissue integrating sensor embodiment in which the sensing moieties are embedded in the scaffold and FIG. 9B shows an embodiment in which the sensing moieties are attached to the surface of the scaffold.
FIG. 9C depicts an overview of an embodiment including sensing media on the surface and embedded within the sensor.
FIG. 9D depicts a cross-section of an exemplary sensor as described herein.
FIGS. 9E and 9F are overviews of exemplary sensors as described herein including one or more fibers containing sensing moieties.
Figure 9A:
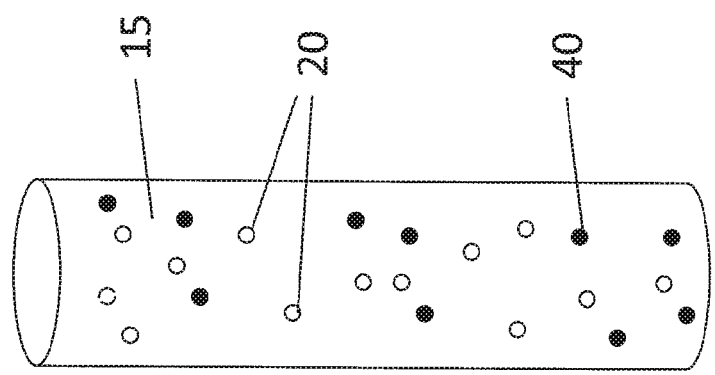
Figure 9C:
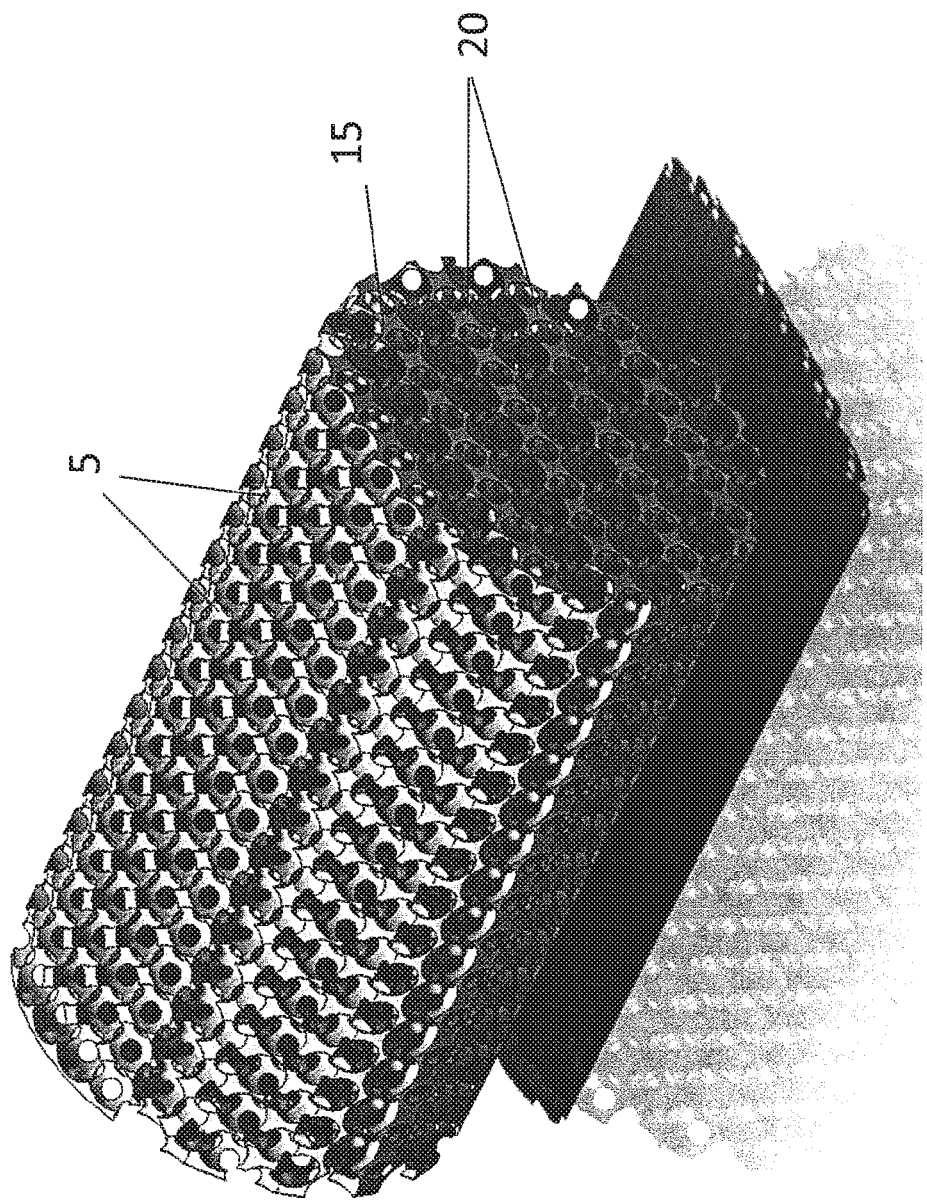
Figure 9E:
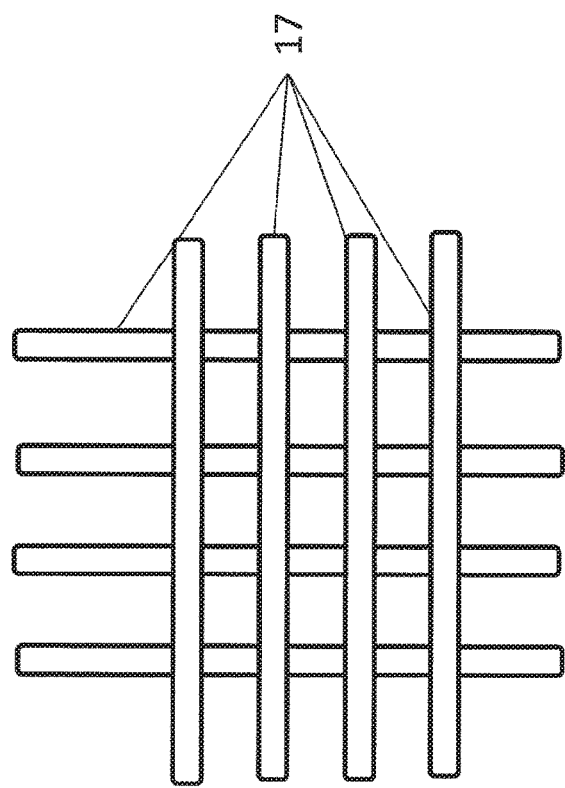
Figure 9F:
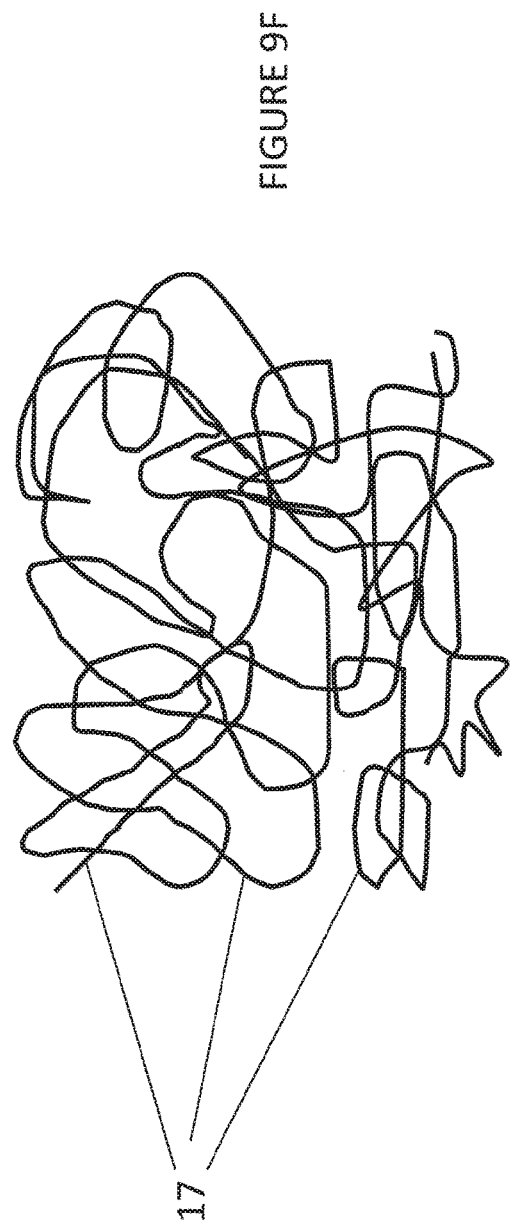
Figure 10B:
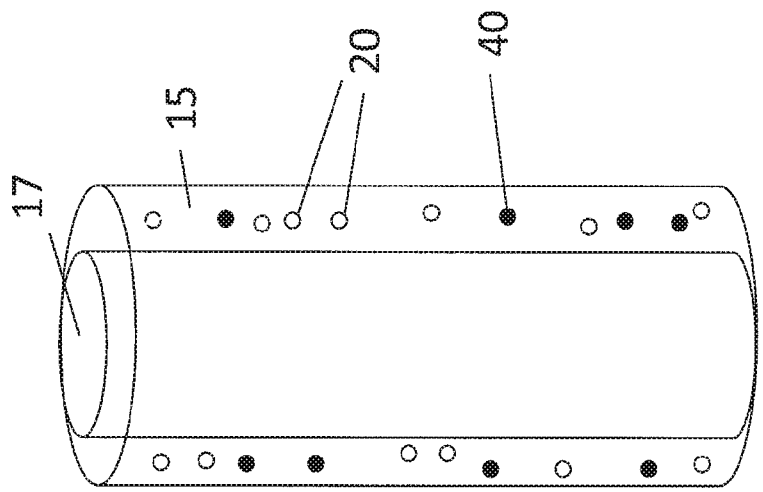
FIG. 10B shows an embodiment with a hollow core and outer layer containing embedded sensing moieties therein.
Figure 10A:
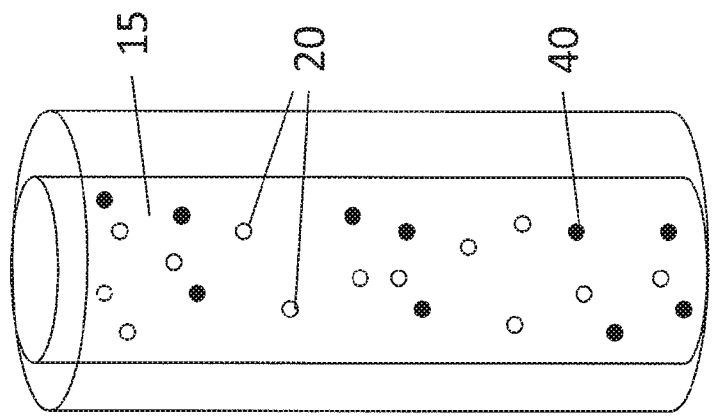
FIG. 10A shows an embodiment with two layers and in which in the sensing moieties are embedded in the inner layer.

FIGS. 9A-F, 10A and 10B are overviews and cross-sections of exemplary tissue-integrating sensors as described herein that are cylindrically shaped. FIG. 9A shows an embodiment that comprises a single layered cylindrical tissue scaffold (or individual fiber) 15 with sensing moieties 20 and additional moieties 40 embedded in the scaffold 15. FIG. 9B shows an embodiment that comprises a single layered cylindrical tissue scaffold (or individual fiber) 15 with sensing moieties 20 attached to the surface of the scaffold 15. FIG. 9C shows an embodiment in which the sensing moieties 20 are attached to the surface and embedded within the scaffold 15. FIG. 9D is a cross section of the exemplary sensors with sensing moieties embedded in the scaffold. FIG. 9E and FIG. 9F show exemplary fibrous embodiments in which the sensors are made up of one or more fibers 17. FIG. 10A shows an embodiment that comprises multiple (two) layers of scaffold material 15 with sensing moieties 20 and additional moieties 40 embedded in the innermost layer of the scaffold 15. FIG. 10B shows an embodiment comprising a hollow interior 17 with an outer layer of scaffold material 15 with sensing moieties and additional moieties 40 embedded in the outer layer. It will be apparent that any number of layers can be used (composed of the same or different materials) and that the sensing moieties (and optional additional moieties) may be present in one, some or all of the layers (and/or on the surface of the scaffold).

FIG. 11 shows a cross-section of an exemplary sensing media as shown in FIG. 9A, including sensing moieties 20 embedded in the tissue-integrating scaffold 15. FIG. 12 is a cross-section of an exemplary sensing media as shown in FIG. 9B and FIG. 13 is a cross-section of an exemplary sensing media as shown in FIG. 12 further including a coating 30 exterior to the sensing moieties 20 attached to the surface of the scaffold 15.

FIG. 14 depicts a cross-section of an exemplary cylindrically shaped sensor implant (whole device) or a portion of an implant (e.g., individual fiber) in which the scaffold 15 is made from polymer where the polymer itself is composed of sensing moieties 20.

Figure 16:
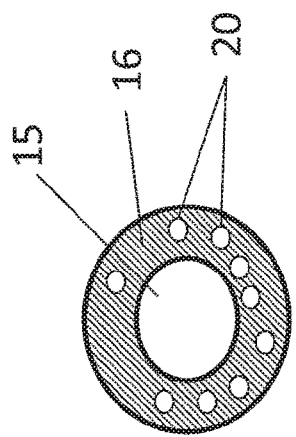
FIG. 16 is a cross-section of an entire (e.g., cylindrically shaped) or portion of (e.g., individual fiber) an exemplary sensing implant including multi-layers, and in which the sensing media are embedded in the outer layer.
Figure 15:
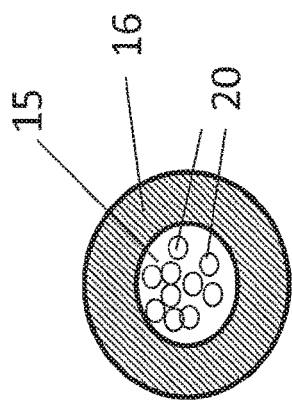
FIG. 15 is a cross-section of an entire (e.g., cylindrically shaped) or portion of (e.g., individual fiber) an exemplary sensing implant including multi-layers, and in which the sensing media are embedded in the inner layer.
Figure 17:
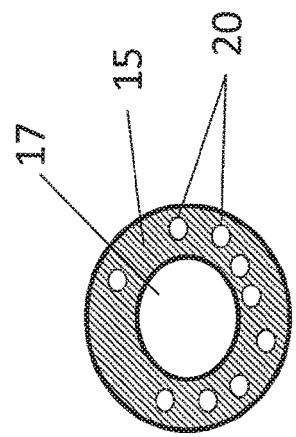
FIG. 17 is a cross-section of an exemplary hollow cylindrically shaped (or individual fiber of a) sensor in which the sending media is embedded in the layer surrounding the hollow core.

FIG. 15 is a cross-section of an exemplary multi-layered cylindrical sensor implant (or individual fiber of an implant) including two layers of scaffold 15, 16 with sensing moieties 20 embedded in the inner layer 15. The inner 15 and outer 16 layers may be made of the same or different polymers. FIG. 16 is a cross-section of an exemplary multi-layered cylindrical sensor implant including two layers of scaffold 15, 16 with sensing moieties 20 embedded in the outer layer 16. The inner 15 and outer 16 layers may be made of the same or different polymers. FIG. 17 is a cross-section of an exemplary hollow cylindrical sensor implant including a scaffold 15 surrounding a hollow core 17 with sensing moieties 20 embedded in the scaffold 15. Additional layers, without or without sensing moieties, can also be present and may be made of the same or different materials.

Tissue-integrating sensors comprised of one or more cylindrical shaped elements (e.g., fibers) eliminate or greatly reduce the foreign body response as compared to currently available implants. Moreover, the average diffusion distances from the capillary supply to all parts of the sensing media are comparable to native tissue, unlike other known sensors.

It will be apparent that the overall dimensions of the sensing media (implantable sensor) will vary according to the subject and/or the analyte(s) to be measured. Typically, the implant will be between about 0.001 mm to 2 mm in thickness (or any value therebetween) and between 1 mm and 1 cm in diameter (or an equivalent cross sectional area of a non-circular shape, for example length/width) and 15 mm in length or less, for example a disk shaped sensor that is 2 mm or less thick and 10 mm or less in diameter. In certain embodiments, the approximate sensor size is approximately 100-1000 microns in diameter and the length is between 0.25 mm and 10 mm. The size of the tissue-integrating sensing media in disk form is typically 2 mm or less thick and 10 mm or less in diameter.

The injected sensing media may be a single piece of tissue-integrating material, or it may be several pieces or particles of tissue-integrating sensing material. It may be injected with a carrier substance (e.g. saline, PBS with anti-inflammatory drugs or other tissue-response modifiers). Furthermore, the sensing media may be implanted into any part of the subject, including, for example, shoulder, arm, leg, abdomen, etc. Preferably, the sensing media is implanted into the skin, for example, the epidermis, the dermis and or the subcutaneous layer of skin.

Systems

Another aspect of the present invention is a tissue-integrating biosensor system for semi-continuous, continuous and/or long-term use within a mammalian body. A biosensor system as described herein comprises the tissue-integrating biosensor (described above). Other components include one or more of the following: interrogator, illuminator, detector, signal receiver, signal transmitter, signal processing component, energy storage component, data storage component, data transmitter, data display, data processing component and combinations thereof. One or more of these other components may be incorporate into a wearable patch that resides over the sensor to detect the sensor signal, or they may be integrated into a hand held or other device, which is periodically held over the implanted sensor to take the measurement. See, FIG. 18.

Figure 19:
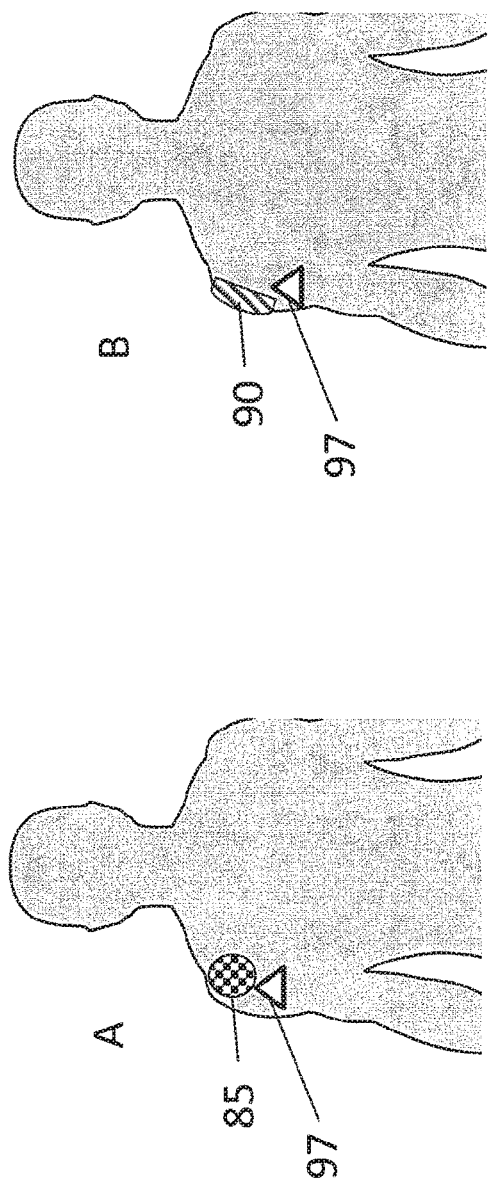
FIG. 19, panels A to C, are schematic representations of exemplary systems including tissue-integrating, vascularizing sensor and interrogators.

FIG. 19 shows exemplary embodiments of a system including an interrogator. FIG. 19A shows a patch 85 including an interrogator and/or detector that may be worn continuously above implanted sensor. FIG. 19B shows a module 90 that can be placed above implanted sensor as desired to interrogate and/or detect continuous or discrete measurements. Non-limiting examples of such modules include hand-held devices such as wands and the like. FIG. 19C depicts how a field 95 that can be used to interrogate (monitor) the subject remotely. Any of the systems described herein may further include an additional component 97 that delivers one or more therapeutics (e.g., analytes) to the subject based on the measurements obtained from the sensor (e.g., an insulin pump that delivers glucose to form a closed loop artificial pancreas). Although depicted separated from the interrogator/detector, it will be apparent that the delivery device 97 may be incorporated into the system (e.g., interrogator and/or detector). The delivery device 97 may be controlled by the operator based on the measurements from the sensor or may be controlled by the data reader directly (e.g., smart phone) or remotely (e.g., telemedicine).

The tissue-integrating scaffold combined with (or comprised of) the one or more sensing moieties are the necessary elements in the tissue-integrating sensor system. Thus, the combination of analyte sensing moieties with tissue-integrating scaffolds comprises the tissue-integrating sensor that is implanted in the body. This tissue-integrating sensor is one component of the biosensor system for continuous monitoring or long-term use within the mammalian body. Other components, including, for example, means to read the signal coming from the tissue-integrating biosensor, show, collect and/or transmit the signal coming from the implanted biosensor. In certain embodiments, the signal is read directly by the human eye. In other embodiments, the signal reader comprises one or more of the following: a hand-held device that detects biosensor signals; a removable patch that resides over the area of the tissue integrating biosensor to continuous or semi-continuous detection of biosensor signals; an implant near, but not touching the tissue-integrating sensing media and/or an implant near and touching a portion of the tissue-integrating sensing media.

The implant may send signal to a watch, a cell phone, a hand-held device, a computer or other data collection and/or read-out device, either directly or, alternatively, via the signal reader. The data may or may not first be processed before sending to these devices and/or these devices may process data received. Data may further be relayed to a database, an email account a cell phone or other storage, processing or display.

The invention works by means of chemical, physical and biological interactions. The tissue-integrating scaffold promotes capillary in-growth into or nearby the sensing scaffold (FIG. 2). Small molecules that diffuse in the interstitial space (e.g. glucose, urea, lactate, pyruvate, glycerol, glutamate, cortisol, acetone, ethanol and other molecules) also diffuse to the surface and/or into the tissue-integrating scaffold and have some interaction with the sensing moieties. In one embodiment, the tissue integrating scaffold is composed of a biomaterial that has sensing moieties contained and/or attached on the exterior of the scaffold. When the analyte diffuses to the surface and interacts with the sensing moieties, a measurable signal is produced (e.g. fluorescence), which is the measured by a detector (signal reader) that is inside or outside the body, but not immediately touching the tissue-integrating biosensor. In another embodiment, the tissue integrating scaffold is composed of a polymer with mesh size large enough to permit molecules of interest to diffuse inside the scaffold. The sensing moieties are contained within the polymer scaffold. When the analyte diffuses into the hydrogel of the tissue-integrating scaffold and interacts with the sensing moieties, a measurable signal is produced (e.g. fluorescence), which is the measured by a detector (signal reader) that is inside or outside the body, but not immediately touching the tissue-integrating biosensor.

In another embodiment, the tissue-integrating scaffold is composed of a polymer with mesh size large enough to permit molecules of interest to diffuse inside the scaffold. The sensing moieties compose the polymer scaffold. When the analyte diffuses into the tissue-integrating scaffold and interacts with the sensing moieties of the scaffold, a measurable signal is produced (e.g. fluorescence), which is the measured by a detector that is inside or outside the body, but not immediately touching the tissue-integrating biosensor.

It will be apparent that one or more analytes can be assayed, and that these analytes are selected by the operator, for example, based on the recommendation of medical personnel, based on interest of monitoring of health and well-being, based on specific biological threats, or based on any other rationale for which the subject has interest to monitor analytes continually or periodically. Typically, the subject would inject, have injected, implant or have implanted the tissue-integrating biosensor or biosensors for the specific analyte or analytes of interest in the tissue to be monitored. The implant can be placed anywhere in the subject. In certain embodiments, the sensing media is injected into the skin (e.g., the dermis or subcutaneously). In other embodiments, the sensor is integrated into alternative spots, including, but not limited to, muscle, visceral fat, peritoneal cavity, gums, cheek, eye, etc.

Figure 18:
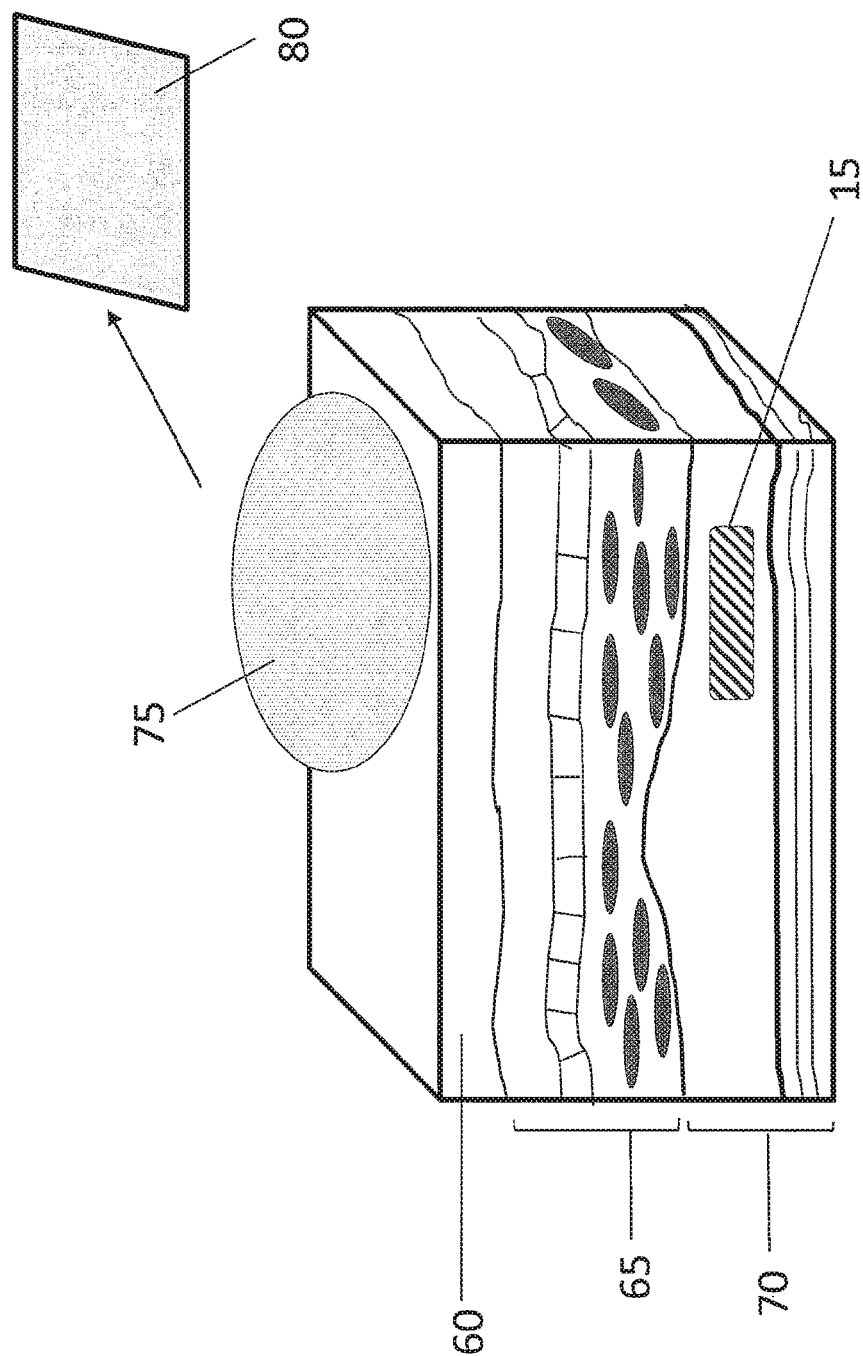
FIG. 18 is a schematic cross-section depiction of a sensing media implant as described herein following implantation into the skin of a subject.

FIG. 18 is a schematic cross-section of a skin sample showing an exemplary embodiment in which the sensing media (tissue integrating implant) 15 is implanted into the subcutaneous tissue 70 of a subject's skin. Also shown are the epidermis 60, the dermis 65 and an optional signal reader 75, depicting as a patch on the surface of the skin. In this embodiment, the detector patch sends interrogation light to the tissue integrating sensing media. The sensing moieties contained in the tissue-integrating sensing media 15, provide a measurable signal (e.g., fluorescence, luminescence, magnetic, etc.) in a manner dependent on the concentration of the analyte(s) of interest. The signal (e.g., fluorescent light) is detected by the detector patch (signal receiver) 75. Also shown in FIG. 18 is optional data reader device 80 that can receive process and/or display information received from the signal reader 75 (e.g., patch). Non-limiting examples of data readers include cell phones, smart phones, watches, computers, and the like. Data may be further relayed to a database, an email account, a cell phone or other storage, processing or display.

The data obtained with the tissue-integrating biosensor system is used by persons to better understand and manage body chemistries (e.g., glucose in the case of diabetics, urea in the case of dialysis patients) and health status.

Methods have long been sought for creating long-lasting in vivo analyte sensors. Reliable, consistent, and continuous sensor data can improve patient care. For example continuous glucose sensors are of great interest to populations with diabetes, and it has been shown that continuous glucose monitoring significantly improves health outcomes (The Juvenile Diabetes Research Foundation Continuous Glucose Monitoring Study Group). Other analytes such as lactate, pyruvate, glycerol, cortisol, urea, dopamine, serotonin, glutamate, ions, hormones, cytokines, insulin, PSA, C reactive protein, biomarkers and a myriad of other analytes are of interest for monitoring of health. Currently, blood samples are withdrawn and analyzed in the lab for various analytes. More recently, bedside or hand-held analyzers for some substances can give more immediate data in close proximity to the patients with quick turn-around time. Even more desirable is the ability to continually monitor analytes of interest to detect changes in states of health.

In addition to substances naturally produced in the body, real-time monitoring of exogenous substances is of interest. For example, over the course of administration of drugs or chemotherapeutic agents that have narrow ranges of effective concentration, in vivo monitoring can provide the clinician with feedback upon which to make adjustments to dosing to assure proper concentrations are achieved and maintained. Constant monitoring of food additives, sodium, alcohol, caffeine, nicotine, vitamin levels, lead, pesticides and a variety of other substances can help individuals and caregivers understand their intake and exposure to certain chemicals and to take control of their own health.

Thus, the tissue-integrating biosensors can be used in the for personal monitoring, physician monitoring of patients, clinical research, animal research studies, and veterinary health for continuously or semi-continuously monitoring analyte concentrations inside a living body. Non-limiting examples of uses of the sensors include for monitoring of diabetic health, dehydration, hemodialysis, acute respiratory distress, stress assessment, congestive heart failure, metabolism status, lifestyle, fitness and training, peripheral vascular resistance, hyonatramia, acute decompensated heart failure, fertility status (e.g., ovulation cycle), cancer detection (early, recurrent, etc.), inflammatory responses (various types), therapeutic drug, including drug concentrations or drug response indicators, ethanol for example for alcoholism treatment, infection disease monitoring, pesticide monitoring, heavy metal monitoring and the like.

In vivo tissue-integrating biosensors for endogenous and exogenous analytes can be used day and night at home and during daily activities (work, exercise, meals, etc.). They can also be used in a care giving setting (e.g. hospital). They may be used in a continuous or intermittent fashion.

Unlike current biosensors, the sensors (also termed sensing media) described herein integrates with the tissue in which it is implanted. The tissue integrating sensing scaffold promotes capillary growth directly into the sensor itself unlike all other marketed sensors or sensors in development (that are known to the authors at the time of submitting this patent).

Methods

Another aspect of this invention is a method for making tissue-integrating sensors. The method(s) for creating a tissue-integrating sensor comprises a process for combining the sensing moieties and the tissue-integrating scaffold in a manner that preserves the integrity of the sensing moieties sufficiently such that they produce measurable signal(s) in response to the analyte of interest.

It will be apparent that the relative amounts of scaffold, sensing moieties and/or reference moieties in the sensor will depend on the polymers and sensing moieties used. For example, in certain embodiments, the sensor will be made with between about 2-95% vol/vol of a monomer or polymer (e.g., 2-85% vol/vol HEMA). Likewise, when present, the amount of cross-linker used will depend on the polymer, for example typically about 0.1 and 10% vol/vol of TEGDMA may be used. Water and or other solvents may be present in any amount (e.g., 5-95% vol/vol water or polyethylene glycol). Initiators may also present in any amount, for example 0.35 to 5% vol/vol of Irgacure. Sensing moieties may be present in any suitable amount, for example, oxygen sensing porphyrins (PdP) may be included at a concentration of about 200 nM to 1 nM. See, also, Example 1.

In some embodiments, the methods of the invention involve a tissue-integrating sensor that is formed by embedding or containing the sensing moieties within the tissue-integrating scaffold. The process may begin with combining the sensing moieties and the scaffold precursor (e.g. monomer, polymer beads, etc.), followed by the formation of the scaffold (e.g. polymerization around template beads, multiphoton polymerization, electrospinning, micro- and nano-printing fabrication techniques, polymer foaming, salt leaching, etc.) and the removal of any residuals (e.g. dissolution of template beads, removal of unpolymerized monomers, etc.).

Non-limiting exemplary methods for embedding or containing the sensingmoieties within the tissue-integrating scaffold include (but are not limited to): polymerization around template beads with or without subsequent dissolution, matrix or other structure, polymerization of a three-dimensional structure using multiphoton polymerization or 3D printing, electrospinning of small fibers, sintering or melting scaffold precursor structures, or swelling scaffold to permit entry of sensing moieties followed by shrinking of scaffold. In certain embodiments, the method comprises polymerizing glucose sensing moieties (nanospheres) into an inverted crystal colloid (ICC) scaffold. For example, glucose-sensing nanospheres are mixed with ICC scaffold pre-polymer during polymerization, causing the nanospheres to be integrated into the pHEMA scaffold as detailed in EXAMPLE 1.

In other embodiments, the tissue-integrating sensor is formed by immobilizing (conjugation or physical entrapment) the sensing moieties on (or to) the surface of the tissue-integrating scaffold. The process begins with an existing scaffold (e.g. extracellular matrix) or the forming of a scaffold (e.g. ICC, synthetic or processed ECM or PoreX Medpore), followed by the attachment of the sensing moieties to the scaffold. The method may also include a coating step that protects or holds in place (e.g. physical entrapment) the sensing moieties to the scaffold. The coating may have the added benefit(s) of (1) protecting the surface chemistry from degradation (e.g. proteases); (2) a diffusion barrier (surface fouling); (3) improving the biocompatibility (e.g. PEG, chitosan, pHEMA, etc.); (4) altering or improving the surface characteristics (e.g. smoothness, pore size, hydrophilicity, etc.). The method may also include step(s) for the sterilization of the tissue-integrating sensor prior to implantation (e.g. ethylene oxide gas, radiation) or in vitro use. Exemplary methods for immobilizing the sensing moieties on the tissue-integrating scaffold include, but are not limited to: conjugation chemistry, adsorption, electrostatics and covering with a continuous coating. Exemplary coatings include PEG, pHEMA and chitosan.

In still further embodiments, the tissue-integrating sensor is formed by constructing a tissue-integrating scaffold made of the sensing moieties. The procedure begins with the sensing moieties of some physical dimension smaller than the desired scaffold features that are then processed into the tissue-integrating material or tissue-integrating precursor. Sensing particles may be bonded together in a tissue-integrating structure through heat or chemical bonds. Pre-polymer solution composed of the sensing moieties may be crosslinked in the desired scaffold structure. Exemplary methods for constructing a tissue-integrating scaffold made OF the sensing moieties include, but are not limited to: bonding the sensing particles using heat, pressure or polymerization; electrospinning, thermal or UV initiated crosslinking of sensing polymers into a tissue integrating structure, including multiphoton polymerization.

In additional embodiments, a sensing media as described herein is formed by tissue-integrating scaffold particles. The process begins with deconstructing a tissue-integrating scaffold into particles that maintain their tissue-integrating properties. The particles are mixed with the sensing moieties and then reconstructed into desirable scaffold form and function. One example is the particulation, e.g., extraction and powdering, of extracellular matrix (ECM) to create particles. The ECM particles are then combined with selected sensing moieties. The mixture may be injected as is or may be combined with a crosslinking agent or polymer (e.g. pHEMA) to add mechanically stability.

In some embodiments, a sensor that is formed by constructing simple or multi-layer fiber(s) implants. The sensing moiety is part of one or more of the base materials from which the fiber scaffold is created or the sensing moiety(ies) are contained or compose one of the layers of sequential building up layers. Some example processes for producing such multi-layers fibers and/or for creating the layers on top of already formed fibers is extrusion, electrospinning, dip coating, spray forming, printing, stamping, rolling, multiphoton polymerization and plasma deposition.

In forming any of the tissue-integrating sensors as described herein, the methods may also include step(s) for the sterilization of the tissue-integrating sensor prior to implantation (e.g. ethylene oxide gas) or in vitro use.

EXAMPLES

Example 1: Production of an Oxygen Sensing Media with Oxygen Sensitive Dye Immobilized in a Hydrogel Scaffold The following describes one proposed method for making a tissue-integrating sensor as described herein. This method involves the use of non-crosslinked PMMA templating microspheres and pHEMA as the scaffold material. The PMMA microsphere template was prepared using sieved PMMA spheres (36 um with a CV less than 5%) and placing the template beads between two glass slides with Teflon spacers. The sintering process included sonicating for at least 10 minutes (one or more times) to closely pack the beads. Following sonication, the template is heated to a sufficient temperature for a sufficient time to fuse the beads (for example, heat to approximately 177° C. for 24 hours).

The general preparation of an oxygen sensing poly(2-hydroxyethyl methacrylate) (pHEMA) scaffold was performed as follows: HEMA 2-hydroxyehtyl methacrylate (56.9% vol/vol), TEGDMA(triethyleneglycol-dimethacrylate) (2.7% vol/vol), ethylene glycol (16.7% vol/vol), water (16.7% vol/vol), the photoinitiator Irgacure 651 (0.2% voV-vol) and 6.7% vol/vol of a 5 mM solution of Pd(II) meso-Tetra(4-carboxyphenyl)porphine (PdP) were mixed, yielding a final concentration of 335 uM PdP in the polymer precursor solution. Polymer, solvents and sensing reagents were mixed as described to achieve sufficiently high sensing chemistry concentration to measurably detect a change in signal through tissue.

The pre-polymer solution was filled into the PMMA. The solution was placed under vacuum to remove any bubbles and completely infiltrate the PMMA-mold and then polymerized by exposing the mold to UV for 5-10 minutes. Next, the PMMA microspheres were dissolved by frequent exchange of dichloromethane or other solvent system for 24-48 hours using a Soxhlet extractor or frequent volume changes.

Implants comprising reference moieties were also prepared as described above except instead of porphyrins, qtracker 800 quantum dots (Invitrogen, 50-800 nM) were included in the scaffold.

The oxygen sensing media and reference moieties were injected with a trocar approximately 2 mm under the surface of mice skin (in different locations on the animal). Mice were imaged with Caliper whole animal imaging system (IVIS™) with an excitation of 535 nm and emission light was collected at 760 nm under oxygenated and deoxygenated conditions.

Figure 20:
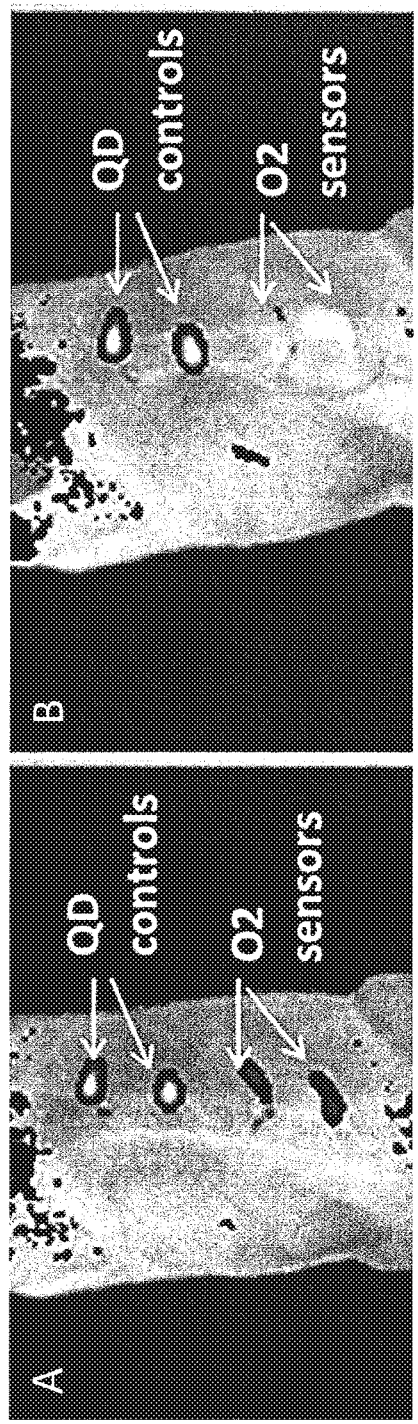
FIG. 20, panels A and B, show photographs of subjects (mice) comprising oxygen sensing media ("OD") as described herein and reference moieties ("QD") produced with reference implants comprising qtracker 800 quantum dots from Invitrogen. Implants were injected with a trocar approximately 2 mm under the surface of mice skin. Mice were imaged with Caliper whole animal imaging system (IVIS™) with an excitation of 535 nm and emission light was collected at 760 nm under oxygenated (FIG. 20A) and deoxygenated conditions (FIG. 20B). As shown, the reference implants (comprising reference moieties) ("QD") maintained their signal in deoxygenated conditions, whereas the oxygen sensing media ("OD") modulated with oxygen concentration.

As shown in FIG. 20, both the oxygen sensing implant ("O2") and the reference moieties ("QD") produced a signal under oxygenated conditions (FIG. 20A). However, under deoxygenated conditions, only the reference moieties produced a detectable signal (FIG. 20B).

Example 2: Production of a Glucose Sensing Media with Glucose Sensitive Assay Immobilized in a Hydrogel Scaffold The following describes one method for making a tissue-integrating sensor as described herein. This method involves the use of non-crosslinked PMMA templating microspheres and pHEMA as the scaffold material. The PMMA microsphere template was prepared using sieved PMMA spheres (36 um with a CV less than 5%) and placing the template beads between two glass slides with Teflon spacers. The sintering process included sonicating for at least 10 minutes (to closely pack the beads), then heating the template to 177° C. for 24 hours to fuse the beads (the conditions will vary for different ovens and may also vary for different batches of beads).

The preparation of glucose sensing poly(2-hydroxyethyl methacrylate) (pHEMA) scaffolds was done as follows. The polymer precursor solution was prepared by mixing HEMA 2-hydroxyethyl methacrylate (57.1% % vol/vol), TEGDMA (triethyleneglycol-dimethacrylate) (2.9 v % vol/vol), ethylene glycol (14.8% vol/vol) water (25.1% vol/vol) and the photoinitiator Irgacure 651 (0.2% vol/vol). Next, the dye/enzyme solution was prepared by adding 5 mg of glucose oxidase enzyme (GOx) and equimolar catalyze in 100 uL of DI water and then adding 100 uL of 1.5 mM Pd(II) meso-Tetra(4-carboxyphenyl)porphine (PdP) in DMSO. The polymer precursor solution and the dye/enzyme solution were combined in a 1:1 ratio for a 39 uM final concentration of GOx and 375 uM PdP. The pre-polymer solution was filled into the mold and placed under vacuum to remove any bubbles and completely infiltrate the PMMA-mold and then polymerized by exposing to UV for 5-10 minutes. Next the PMMA microspheres were dissolved by frequent exchange of dichloromethane or other solvent system for 24-48 hrs using a Soxhlet extractor or frequent volume changes.

Disk of the glucose sensor scaffold material were punched from the rectangular pieces (microscope slide-shape) and fixed inside an automated flow-through system with a built in flourimeter. Glucose solutions (in PBS) of various concentrations were flowed over the sensor scaffold discs and fluorescence and lifetime readings were collected at various glucose concentrations over successive runs (e.g., PdP emission was measured as a function of glucose concentration).

Figure 21:
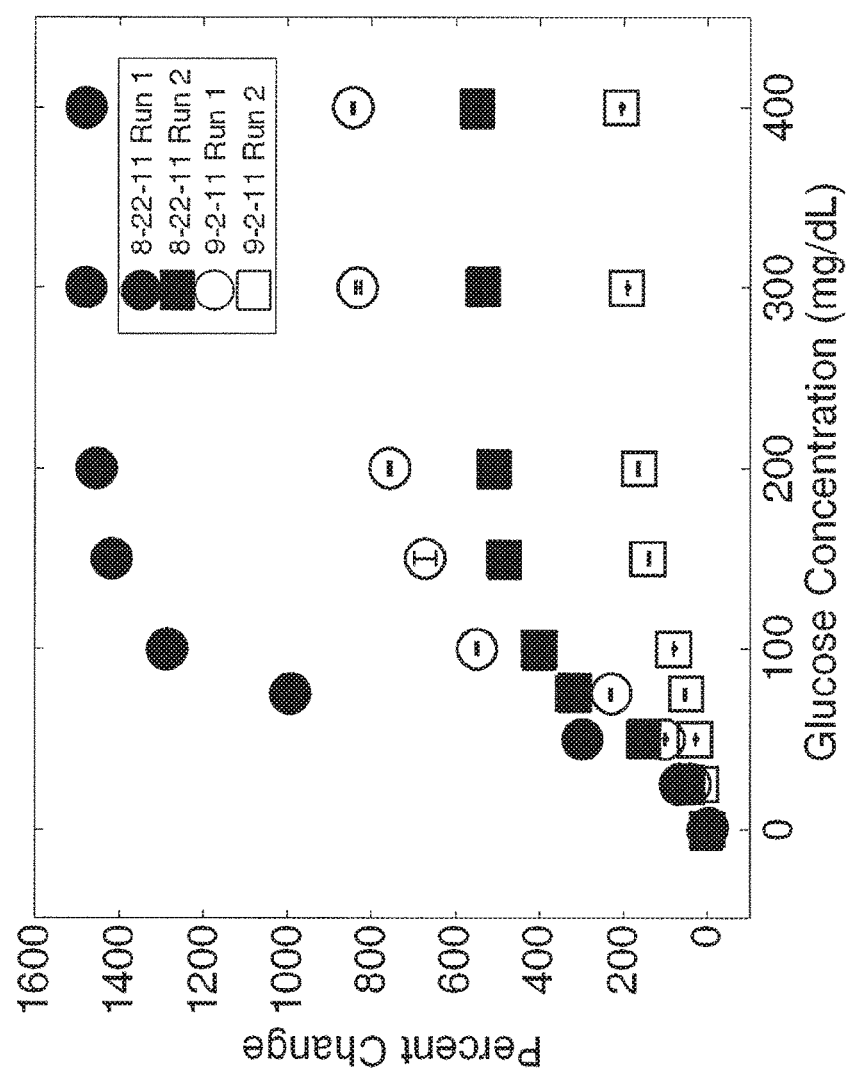
FIG. 21 is a graph depicting glucose monitoring from glucose sensors as described herein (Example 2). Data show percent change of PDP emission as a function of glucose concentration. Disk of glucose sensor scaffold material were punched from the rectangular pieces (microscope slide-shape) that were produced as described in Example 2. Sensor scaffold discs were fixed inside an automated flow-through system with a built in flourimeter. Glucose solutions (in PBS) of various concentrations were flowed over the sensor scaffold discs. Fluorescence and lifetime readings were collected at various glucose concentrations over successive runs. A plot of the change in sensor signal compared to baseline (zero glucose concentration) is shown below.

As shown in FIG. 21, the signal emitted from the sensor modulated in response to glucose concentration.

Example 3: Production of an Analyte Sensing Media with Analyte Sensitive Dye Immobilized in a Hydrogel Scaffold The following describes one proposed method for making a tissue-integrating sensor as described herein. This method involves the use of non-crosslinked PMMA templating microspheres and pHEMA as the scaffold material. The PMMA microsphere template is prepared using sieved PMMA spheres (36 um with a CV less than 5%) and placing the template beads between two glass slides with Teflon spacers. The sintering process includes sonicating for 10 minutes (to closely pack the beads), then heating the template to 177° C. for 24 hours to fuse the beads (the conditions will vary for different ovens and may also vary for different batches of beads).

Polymer pre-cursor that will form the hydrogel scaffold is then prepared. The general preparation of poly(2-hydroxyethyl methacrylate) (pHEMA) scaffold is as follows: In separate vials, two solutions are prepared: 0.89 ml of a 20% solution of APS (ammonium persulfate) in water and 0.3 ml of a 15% solution TEMED (tetramethylethylenediamine) in water. To a third vial the HEMA 2-hydroxyehtyl methacrylate (9.26 ml), TEGDMA(triethyleneglycol-dimethacrylate) (0.46 ml), ethylene glycol (2.6 ml) and water (2.68 ml) are added by volume measurement and mixed.

The TEMED solution is added to the main pre-polymer vial. Sensing nanospheres ranging from 2-95% volume of the total reactant volume (e.g. 5 ml of 100-200 nm alginate nanospheres containing fluorescent glucose sensing chemistry) are mixed with the pre-polymer solution. The pre-polymer solution is filled into the mold and then the APS solution added. The solution is placed under vacuum to remove any bubbles and completely infiltrate the PMMM-mold and then polymerized at room temperature for one hour. Next, the PMMA microspheres are dissolved by frequent exchange of dichloromethane or other solvent system for 24-48 hrs using a Soxhlet extractor or frequent volume changes.

Example 4: Implantation

A tissue integrating sensor produced in rods that are 300-500 um in diameter and 5 mm long are placed in a 19-23 Gauge insertion needle, trochar, modified biopsy device or other devices engineered for injection under the skin. The sensor is optionally dehydrated or compressed before insertion to allow for the use of a smaller insertion needle.

Upon insertion, skin is pinched up so that the insertion needle is placed parallel to the surface of the skin 1-4 mm beneath the surface. Fluid or a reverse displacement plunger (or trochar) is used to leave the sensor in the tissue as the syringe is withdrawn. Insertion site may include any subcutaneous area, typically the abdomen, arm and thigh.

Example 5: Measurement

Data from the sensor collected, processed and displayed on a smart phone, other hand-held device, computer screen or other visualization format, for example using commercially available data display devices available for example from Medtronic. Raw data is converted to an analyte concentration or some non-quantitative representation of the analyte concentration (e.g. high, low, within range). Values at any given point in time or trends (graphs over time) or summary statistics over a period of time are provided. An indication of the quality of the data is optionally provided.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A tissue-integrating sensor for detecting an analyte, consisting of:
    a hydrogel scaffold defining a plurality of hollow, interconnected pores such that capillaries can grow directly into the hydrogel scaffold; and
    one or more sensing moieties disposed within the hydrogel scaffold, a sensing moiety from the one or more sensing moieties configured to produce a signal in a presence of an analyte.

2. The tissue-integrating sensor of claim 1, wherein the hydrogel scaffold consists of the sensing moiety.

3. The tissue-integrating sensor of claim 1, wherein the sensing moiety and the hydrogel scaffold, collectively, are homogenous.

4. The tissue-integrating sensor of claim 1, wherein the plurality of hollow, interconnected pores are configured such that capillaries can grow in close proximity to the one or more sensing moieties in all regions of the tissue-integrating sensor.

5. The tissue-integrating sensor of claim 1, wherein the plurality of hollow, interconnected pores are configured such that, when the tissue-integrating sensor is placed into a tissue of a subject, capillaries can grow into the hydrogel scaffold such that an average distance from any point of the tissue-integrating sensor to a first blood vessel is no greater than 100 microns more than an average distance from any point in the tissue into which the tissue-integrating sensor is placed to a second blood vessel.

6. The tissue-integrating sensor of claim 1, wherein:
    the tissue-integrating sensor is configured to be placed directly into a tissue of a subject devoid of additional sensor elements;
    the tissue-integrating sensor alone is configured to be illuminated by an excitation light produced by an interrogator while the tissue-integrating sensor is within the tissue of the subject, and the interrogator is external to the subject's body; and
    the tissue-integrating sensor alone is configured to produce the signal in response to the excitation light such that the signal is detectable by a detector external to the subject's body.

7. The tissue-integrating sensor of claim 1, wherein the tissue-integrating sensor is configured to contact only tissue when the tissue-integrating sensor is placed into a tissue of a subject.

8. The tissue-integrating sensor of claim 1, wherein the tissue-integrating sensor is cylindrical.

9. The tissue-integrating sensor of claim 1, wherein the tissue-integrating sensor is cylindrical and has a diameter of 500 micrometers or less.

10. The tissue-integrating sensor of claim 1, wherein the one or more sensing moieties are configured to produce the signal in the presence of the analyte in vivo.

11. The tissue-integrating sensor of claim 1, wherein:
    the tissue-integrating sensor is configured to be implanted in a subcutis of a subject; and
    the signal produced by the one or more sensing moieties is configured to be detected by a detector external to an epidermis of the subject.

12. The tissue-integrating sensor of claim 1, wherein the hydrogel scaffold is an inverse colloid crystal.

13. The tissue-integrating sensor of claim 1, wherein the plurality of hollow, interconnected pores are constructed by dissolving sintered microparticles.

14. The tissue-integrating sensor of claim 1, wherein the signal is an optical signal.

15. The tissue-integrating sensor of claim 1, wherein:
the tissue-integrating sensor is configured to be placed directly into a tissue of a subject;
the tissue-integrating sensor alone is configured to be illuminated by an excitation light produced by an interrogator while the tissue-integrating sensor is within the tissue of the subject and the interrogator is external to the subject's body; and
the tissue-integrating sensor alone is configured to produce the signal in response to the excitation light such that the signal is detectable by a detector external to the subject's body.

16. The tissue-integrating sensor of claim 1, wherein the hydrogel scaffold has a single layer.

17. An apparatus, comprising:
a hydrogel, tissue-integrating scaffold defining a plurality of hollow, interconnected pores configured such that capillaries can grow directly into the hydrogel, tissue-integrating scaffold; and
a sensing moiety included within the hydrogel, tissue-integrating scaffold, the sensing moiety configured to produce a signal in a presence of an analyte.

18. The apparatus of claim 17, wherein the hydrogel, tissue-integrating scaffold is configured to be placed in direct contact with a tissue of a subject.

19. The apparatus of claim 17, wherein the hydrogel, tissue-integrating scaffold has a cylindrical shape.

20. The apparatus of claim 19, wherein an entirety of a periphery of the hydrogel, tissue-integrating scaffold is configured to be placed in direct contact with a tissue of a subject.

21. The apparatus of claim 17, wherein the entire apparatus is configured to be placed into a tissue of a subject, the apparatus being devoid of electronics.

22. The apparatus of claim 17, wherein hydrogel of the hydrogel, tissue-integrating scaffold is permeable to the analyte.

23. The apparatus of claim 17, wherein the hydrogel, tissue-integrating scaffold is constructed entirely of one or more sensing moieties, the sensing moiety being from the one or more sensing moieties.

24. The apparatus of claim 17, wherein the hydrogel, tissue-integrating scaffold has a cylindrical shape having a diameter of 500 micrometers or less.

25. The apparatus of claim 17, wherein the sensing moiety is a stimuli-sensitive polymer.

26. The apparatus of claim 17, wherein the signal is an optical signal.

27. The apparatus of claim 17, wherein the hydrogel, tissue-integrating scaffold has a single layer.

28. A tissue-integrating sensor for detecting an analyte, consisting of:
a hydrogel scaffold having a single layer defining a plurality of interconnected pores such that capillaries can grow directly into the hydrogel scaffold;
one or more sensing moieties disposed within the hydrogel scaffold, a sensing moiety from the one or more sensing moieties configured to produce a signal in the presence of an analyte; and
one or more calibration moieties disposed within the hydrogel scaffold, a calibration moiety from the one or more calibration moieties configured to produce a signal when illuminated by an excitation light.

* * * * *